US008420791B2

(12) United States Patent
Ebert et al.

(10) Patent No.: US 8,420,791 B2
(45) Date of Patent: Apr. 16, 2013

(54) EXPRESSION OF FOXP3 BY CANCER CELLS

(75) Inventors: Lisa Michelle Ebert, Northcote (AU); Weisan Chen, Heidelberg (AU); Jonathan S. Cebon, Clifton Hill (AU); Ian Davis, Warrandyte (AU)

(73) Assignee: Ludwig Institute for Cancer Research Ltd., New York, NY (US)

( * ) Notice: Subject to any disclaimer, the term of this patent is extended or adjusted under 35 U.S.C. 154(b) by 448 days.

(21) Appl. No.: 12/312,472

(22) PCT Filed: Nov. 27, 2007

(86) PCT No.: PCT/US2007/024388

§ 371 (c)(1), (2), (4) Date: Feb. 5, 2010

(87) PCT Pub. No.: WO2008/066784

PCT Pub. Date: Jun. 5, 2008

(65) Prior Publication Data

US 2010/0143359 A1 Jun. 10, 2010

Related U.S. Application Data

(60) Provisional application No. 60/997,173, filed on Oct. 1, 2007, provisional application No. 60/861,185, filed on Nov. 27, 2006.

(51) Int. Cl.
*C07H 21/02* (2006.01)

(52) U.S. Cl.
USPC .......................................................... 536/23.1

(58) Field of Classification Search ......................... None
See application file for complete search history.

(56) References Cited

U.S. PATENT DOCUMENTS 6,414,129 B1 * 7/2002 Brunkow et al. ............ 536/23.5
2006/0002932 A1 1/2006 Vieweg

FOREIGN PATENT DOCUMENTS

WO WO 02/090600 A2 11/2002
WO WO 2005/010215 A2 2/2005
WO WO 2006/074370 A2 7/2006

OTHER PUBLICATIONS

Allan et al (JCI, 2005, 115(11): 3276-3284).*
Allan et al (The Journal of Clinical Investigation, 2005, 115(11): 3276-3284).*
[No Author Listed] "Fox Antibodies Optimized for Flow Cytometry, IHC, WB for Mouse, Human, Rat, Non-Human Primates & Canine." EBioscience. 2008. Retrieved from http://www.ebioscience.com/ebioscience/whatsnew/Foxp3/Foxp3.htm#references. Retrieved on Aug. 6, 2008. 8 pages.
Ebert et al., The regulatory T cell-associated transcription factor FoxP3 is expressed by tumor cells. Cancer Res. Apr. 15, 2008;68(8):3001-9.
Gupta et al., Expression of Foxp3 and vascular endothelial growth factor in human breast cancer: its correlation with angiogensis and disease progression. Eur J Cancer. Supp. 2006;4(2):126. Abstract No. 271.
Hinz et al., Foxp3 expression in pancreatic carcinoma cells as a novel mechanism of immune evasion in cancer. Cancer Res. Sep. 1, 2007;67(17):8344-50.
Ishibashi et al., Expression of Foxp3 in non-small cell lung cancer patients is significantly higher in tumor tissues than in normal tissues, especially in tumors smaller than 30 mm. Oncol Rep. May 2006;15(5):1315-9.
Lim et al., Cutting edge: direct suppression of B cells by CD4+ CD25+ regulatory T cells. J Immunol. Oct. 1, 2005;175(7):4180-3.
Raluy et al., Tumor immunological significance of the T-reg marker FoxP3 in malignant epithelial cells of the pancreas. Immunobiology. 2005;215(6-8):474-75. Joint Annual Meeting of the German and Scandinavian Societies of Immunology. Sep. 21-24, 2005, Germany. Abstract J.50.
Smith et al., Splice variants of human FoxP3 are functional inhibitors of human CD4+ T-cell activation. Immunology. Oct. 2006;119(2):203-11.

* cited by examiner

*Primary Examiner* — Sean Aeder
(74) *Attorney, Agent, or Firm* — Wolf, Greenfield & Sacks, P.C.

(57) ABSTRACT

The present invention relates to the treatment, diagnosis, and prophylaxis of cancer based on the expression of foxp3.

5 Claims, 11 Drawing Sheets a b a b

EXPRESSION OF FOXP3 BY CANCER CELLS

RELATED APPLICATIONS

This application is a national stage filing under 35 U.S.C. §371 of international application PCT/US2007/024388, filed Nov. 27, 2007, which was published under PCT Article 21(2) in English, and claims the benefit under 35 U.S.C. §119(e) of U.S. provisional patent application Ser. No. 60/861,185, filed Nov. 27, 2006 and of U.S. provisional patent application Ser. No. 60/997,173, filed Oct. 1, 2007, the contents of which are incorporated herein by reference in their entirety.

FIELD OF THE INVENTION

The present invention relates to the treatment, diagnosis, and prophylaxis of cancer based on the expression of foxp3 in cancer cells.

BACKGROUND OF THE INVENTION

FoxP3 is well-established as the "master gene" that regulates the development and function of CD4+CD25+ T regulatory ($T_{reg}$) cells. Generally, $T_{reg}$ cells represent approximately 5% of the CD4+ T-cells in human blood and are essential in maintaining immune homeostasis via $T_{reg}$ cell-mediated immune suppression, which may lead to tumor immune escape.

The immune system is subject to many levels of control which, together, avert attack on self tissues and limit over-exuberant immune responses to pathogens. In recent years, it has been recognized that distinct populations of T cells with 'regulatory' (or suppressor) function make a major contribution to keeping the immune system in check (1, 2). Amongst these, the best understood is the population of regulatory T cells characterized by constitutive expression of CD25 and the transcription factor FoxP3 (3, 4). These cells, known as Treg, are primarily noted for their ability to block the proliferation and cytokine secretion capacity of other T cells. Suppression is dependent on direct contact with the target cell yet, despite extensive investigation, the primary suppressive mechanisms involved are still unclear. Production of immunosuppressive cytokines such as TGF-β and expression of surface molecules such as CTLA-4 may play a role, but their relative importance remains controversial (5).

Despite an essential role in preventing autoimmunity, Treg can also have a negative impact on health by down-regulating beneficial immune responses such as those mounted against tumors. Numerous studies in animal models have demonstrated that specifically removing or inhibiting Treg dramatically improves tumor clearance and survival (6, 7). Furthermore, a number of reports have documented the presence of Treg within human tumor tissue, and in one of these studies the number of Treg also showed a clear negative correlation with survival (6-10). Thus, Treg may play a major role in preventing the development of effective anti-tumor immunity.

FoxP3 is a member of the forkhead family of transcription factors and, at least in mice, appears to act as a 'master switch' for the development and function of Treg (4, 11). Mice lacking functional expression of FoxP3 completely lack Treg, a deficit which is thought to be responsible for the fatal immunoproliferative disease these mice develop. Moreover, ectopic expression of FoxP3 in conventional mouse T cells endows them with the full phenotype and function of Treg. In humans, there is also a strong association between FoxP3 expression and the Treg phenotype, although the relationship may not be as simple as in mice (11). Mutations in FOXP3 have been associated with the development of a multi-organ autoimmune disorder known as IPEX (immune dysregulation, polyendocrinopathy, enteropathy, X-linked syndrome) (12), suggesting that defects in FoxP3 expression or function lead to impaired Treg development. In keeping with this hypothesis, Treg from these patients have greatly reduced suppressive activity (13). Furthermore, ectopic expression of FoxP3 allows conventional human T cells to acquire many characteristics of Treg, although some studies have shown that their suppressive activity is inferior to that of bona fide Treg (14, 15). Interestingly, while expression of FoxP3 in freshly isolated peripheral blood is limited to Treg, in vitro activation can lead to a transient expression of FoxP3 by conventional T cells; it is currently a matter of debate as to whether or not these cells have regulatory activity (16-18). Thus, whereas FoxP3 is both necessary and sufficient for Treg activity in mice, other factors in addition to FoxP3 may be involved in induction of human Treg activity.

SUMMARY OF THE INVENTION

To date, FoxP3 expression has been thought to be restricted to the T cell lineage (19, 20). In the present study, however, we provide several lines of evidence that—in addition to T cells—FoxP3 is also expressed by tumor cells. Given the central role of FoxP3 in Treg function, the expression of FoxP3 by tumor cells may represent a novel mechanism by which cancers suppress the immune system in order to escape destruction.

We have observed for the first time that FoxP3 expression in tumor tissue was not only restricted to the infiltrating $T_{reg}$, but was also expressed within the tumor cells Therefore, we hypothesized that the expression of FoxP3 during tumorigenesis may result in tumor immunological tolerance. We verified FoxP3 expression in a large number of melanoma cell lines using flow cytometry, reverse-transcriptase PCR and Western blot. Furthermore, we extended the study with tumor cell lines from other organs and demonstrated that the majority expressed FoxP3. In contrast, we showed that normal primary cell lines did not express FoxP3 supporting the association of FoxP3 expression with tumorigenesis. Meanwhile, we discovered a novel third splice isoform of FoxP3 expressed specifically in the brain and reproductive organs, suggesting that these tissues may establish an immune privilege-like site by expressing FoxP3. Our data reveal that tumor cells express FoxP3, hence suggesting that the expression of FoxP3 by tumor cells is crucial as a tool of survival through suppression of anti-tumor immune responses. Ultimately, identifying the origin of tumor evasion is a stepping stone towards manipulating our immune system to eradicate tumor cells.

According to one aspect of the invention, methods for diagnosing cancer in a subject are provided. The methods include obtaining a biological sample from the subject, and determining the expression in the biological sample of a FoxP3 polypeptide or a nucleic acid molecule that encodes the FoxP3 polypeptide. The nucleic acid molecule preferably comprises SEQ ID NO:1, or a nucleotide sequence that is at least 90% identical to the nucleotide sequence of SEQ ID NO:1. The expression in the biological sample of the polypeptide or the nucleic acid molecule that encodes it is indicative of the subject having cancer. The cancer preferably is not pancreatic carcinoma. Preferably the biological sample is free of regulatory T cells ($T_{reg}$; CD4+CD25+FOXP3+).

In some embodiments the step of determining the expression of the polypeptide or the nucleic acid molecule that encodes the polypeptide includes contacting the biological sample with an agent that selectively binds to the polypeptide or the nucleic acid molecule that encodes the polypeptide. In some embodiments the agent is a nucleic acid probe or a nucleic acid primer. Preferably the expression of the nucleic acid molecule is determined by nucleic acid hybridization using the nucleic acid probe or nucleic acid amplification using the nucleic acid primer. In some preferred embodiments the nucleic acid amplification is real-time RT-PCR or RT-PCR. In other preferred embodiments the nucleic acid hybridization is performed using a nucleic acid microarray containing the nucleic acid probe.

In other embodiments the agent is a polypeptide, such as an antibody or antigen-binding fragment thereof, preferably a monoclonal antibody, or a $F(ab')_2$, Fab, Fd, or Fv fragment. In some preferred embodiments the antibody or antigen-binding fragment is labeled with a detectable label, preferably a fluorescent or radioactive label.

In some of the foregoing methods, the sample comprises tissue, cells, and/or blood.

According to another aspect of the invention, methods for diagnosing cancer in a subject are provided. The methods include obtaining a biological sample from the subject, and determining the expression in the biological sample of a FoxP3 polypeptide or a nucleic acid molecule that encodes the FoxP3 polypeptide. The nucleic acid molecule comprises (1) SEQ ID NO:6, foxp3 (SEQ ID NO:1) lacking exons 2 and 3, or a nucleic acid molecule comprising foxp3 exons 1 and 4 joined together, or (2) a nucleotide sequence that is at least 90% identical to the nucleotide sequence of (1). The expression in the biological sample of the polypeptide or the nucleic acid molecule that encodes it is indicative of the subject having cancer. Preferably the biological sample is free of regulatory T cells ($T_{reg}$; CD4+CD25+FOXP3+).

In some embodiments the step of determining the expression of the polypeptide or the nucleic acid molecule that encodes the polypeptide includes contacting the biological sample with an agent that selectively binds to the polypeptide or the nucleic acid molecule that encodes the polypeptide. In some embodiments the agent is a nucleic acid probe or a nucleic acid primer. Preferably the expression of the nucleic acid molecule is determined by nucleic acid hybridization using the nucleic acid probe or nucleic acid amplification using the nucleic acid primer. In some preferred embodiments the nucleic acid amplification is real-time RT-PCR or RT-PCR. In other preferred embodiments the nucleic acid hybridization is performed using a nucleic acid microarray containing the nucleic acid probe.

In other embodiments the agent is a polypeptide, such as an antibody or antigen-binding fragment thereof, preferably a monoclonal antibody, or a $F(ab')_2$, Fab, Fd, or Fv fragment. In some preferred embodiments the antibody or antigen-binding fragment is labeled with a detectable label, preferably a fluorescent or radioactive label.

In some of the foregoing methods, the sample comprises tissue, cells, and/or blood.

According to another aspect of the invention, isolated nucleic acid molecules are provided that are selected from the group consisting of: (a) complements of nucleic acid molecules that hybridize under high stringency conditions to a second nucleic acid molecule comprising a nucleotide sequence set forth as SEQ ID NO:6, foxp3 (SEQ ID NO:1) lacking exons 2 and 3, or foxp3 exons 1 and 4 joined together, (b) nucleic acid molecules that differ from the nucleic acid molecules of (a) in codon sequence due to the degeneracy of the genetic code, and (c) full-length complements of (a) or (b).

In some embodiments the isolated nucleic acid molecule comprises or consists of SEQ ID NO:6. In other embodiments the isolated nucleic acid molecule comprises or consists of foxp3 (SEQ ID NO:1) lacking exons 2 and 3. In still other embodiments the isolated nucleic acid molecule comprises or consists of foxp3 exons 1 and 4 joined together.

According to another aspect of the invention, isolated nucleic acid molecules are provided that include a nucleotide sequence that is at least about 90% identical to a nucleotide sequence set forth as SEQ ID NO:6, foxp3 (SEQ ID NO:1) lacking exons 2 and 3, or foxp3 exons 1 and 4 joined together, or a full-length complement thereof.

In some embodiments the nucleic acid molecule comprises a nucleotide sequence that is at least about 95% identical, preferably at least about 97% identical, more preferably at least about 98% identical, still more preferably at least about 99% identical.

Compositions that include the foregoing isolated nucleic acid molecules and a carrier also are provided, as are compositions that include the foregoing isolated nucleic acid molecules attached to a solid substrate.

According to another aspect of the invention, kits are provided that include one or more of the foregoing nucleic acid molecules that hybridize under high stringency conditions to the isolated foxp3 nucleic acid molecules. In some embodiments the one or more nucleic acid molecules are detectably labeled. In other embodiments the one or more nucleic acid molecules consist of a first primer and a second primer, wherein the first primer and the second primer are constructed and arranged to selectively amplify at least a portion of a nucleic acid molecule that comprises a nucleotide sequence set forth as SEQ ID NO:6, foxp3 (SEQ ID NO:1) lacking exons 2 and 3, or foxp3 exons 1 and 4 joined together.

According to a further aspect of the invention, expression vectors that include the foregoing isolated nucleic acid molecules operably linked to a promoter, and isolated host cells transformed or transfected with these expression vectors also are provided.

According to additional aspects of the invention, isolated polypeptides encoded by the foregoing isolated nucleic acid molecules or that include the amino acid sequence of SEQ ID NO:11 are provided. The invention also provides isolated antibodies or antigen-binding fragments thereof that selectively binds to these isolated polypeptides. In some embodiments the antibody is a monoclonal antibody, a human antibody, a domain antibody, a humanized antibody, a single chain antibody or a chimeric antibody. In other embodiments the antibody fragment is a $F(ab')_2$, Fab, Fd, or Fv fragment. Compositions that include the isolated antibodies or antigen-binding fragments and a carrier also are provided, as are kits that include the isolated antibodies or antigen-binding fragments.

According to another aspect of the invention, siRNA molecules that selectively target SEQ ID NO:6, foxp3 (SEQ ID NO:1) lacking exons 2 and 3, or a nucleic acid molecule comprising foxp3 exons 1 and 4 joined together are provided.

According to still another aspect of the invention, methods for treating or preventing cancer are provided. The methods include administering to a subject in need of such treatment an agent that reduces expression of FoxP3 nucleic acid or polypeptide in the subject, in an amount effective to treat or prevent cancer. Preferably the cancer is not pancreatic carcinoma.

In some embodiments the agent is administered by intratumoral administration. In preferred embodiments the agent is a siRNA molecule or an antisense nucleic acid molecule. Preferably the agent selectively targets SEQ ID NO:6, foxp3

(SEQ ID NO:1) lacking exons 2 and 3, or a nucleic acid molecule comprising foxp3 exons 1 and 4 joined together. In other embodiments, the cancer is a B cell lymphoma.

According to yet a further aspect of the invention, methods for treating or preventing cancer are provided. The methods include administering to a subject in need of such treatment an agent that reduces expression in the subject of a nucleic acid molecule comprising SEQ ID NO:6, foxp3 (SEQ ID NO:1) lacking exons 2 and 3, or a nucleic acid molecule comprising foxp3 exons 1 and 4 joined together, in an amount effective to treat or prevent cancer.

In some embodiments the agent is administered by intratumoral administration. In preferred embodiments the agent is a siRNA molecule or an antisense nucleic acid molecule. Preferably the agent selectively targets SEQ ID NO:6, foxp3 (SEQ ID NO:1) lacking exons 2 and 3, or a nucleic acid molecule comprising foxp3 exons 1 and 4 joined together. In other embodiments, the cancer is a B cell lymphoma.

In a further aspect of the invention, methods for inducing an immune response are provided. The methods include administering to a subject in need of such treatment an agent that induces an immune response to a FoxP3 variant polypeptide lacking exons 2 and 3, in an amount effective to induce an immune response against the FoxP3 variant polypeptide. In some embodiments, the agent is FoxP3 variant polypeptide lacking exons 2 and 3, and/or a peptide comprising an epitope of the FoxP3 variant polypeptide lacking exons 2 and 3. Preferred peptides include the peptides as described in FIG. 12, which can be used singly or in any combination. In some embodiments, the immune response is a CD4 and/or a CD8 response.

In further embodiments of the foregoing methods, the subject has a cancer and the immune response is sufficient to treating or preventing cancer. In preferred methods, the cancer expresses the FoxP3 variant polypeptide lacking exons 2 and 3, which can be detected using methods described herein and well known to persons skilled in the art. In certain embodiments, the cancer is a B cell lymphoma.

According to another aspect of the invention, methods for inhibiting immunological tolerance of tumors are provided. The methods include administering to a subject in need of such treatment an agent that reduces expression of FoxP3 nucleic acid or polypeptide in the subject, in an amount effective to inhibit immunological tolerance of tumors. Preferably the cancer is not pancreatic carcinoma.

In some embodiments the agent is administered by intratumoral administration. In preferred embodiments the agent is a siRNA molecule or an antisense nucleic acid molecule. Preferably the agent selectively targets SEQ ID NO:6, foxp3 (SEQ ID NO:1) lacking exons 2 and 3, or a nucleic acid molecule comprising foxp3 exons 1 and 4 joined together.

According to yet a further aspect of the invention, methods for inhibiting immunological tolerance of tumors are provided. The methods include administering to a subject in need of such treatment an agent that reduces expression in the subject of a nucleic acid molecule comprising SEQ ID NO:6, foxp3 (SEQ ID NO:1) lacking exons 2 and 3, or a nucleic acid molecule comprising foxp3 exons 1 and 4 joined together, in an amount effective to inhibit immunological tolerance of tumors.

In some embodiments the agent is administered by intratumoral administration. In preferred embodiments the agent is a siRNA molecule or an antisense nucleic acid molecule. Preferably the agent selectively targets SEQ ID NO:6, foxp3 (SEQ ID NO:1) lacking exons 2 and 3, or a nucleic acid molecule comprising foxp3 exons 1 and 4 joined together.

According to another aspect of the invention, methods for treating or preventing post-transplant lymphoproliferative disorder (PTLD) are provided. The methods include administering to a subject in need of such treatment an agent that reduces expression of FoxP3 in the subject, in an amount effective to treat or prevent PTLD.

In some embodiments the agent is administered before, during and/or after solid organ or bone marrow transplantation. In preferred embodiments the agent is a siRNA molecule or an antisense nucleic acid molecule. Preferably the agent selectively targets SEQ ID NO:6, foxp3 (SEQ ID NO:1) lacking exons 2 and 3, or a nucleic acid molecule comprising foxp3 exons 1 and 4 joined together.

According to a further aspect of the invention, methods for treating or preventing post-transplant lymphoproliferative disorder (PTLD) are provided. The methods include administering to a subject in need of such treatment an agent that reduces expression in the subject of a nucleic acid molecule comprising SEQ ID NO:6, foxp3 (SEQ ID NO:1) lacking exons 2 and 3, or a nucleic acid molecule comprising foxp3 exons 1 and 4 joined together, in an amount effective to treat or prevent PTLD.

In some embodiments the agent is administered before, during and/or after solid organ or bone marrow transplantation. In preferred embodiments the agent is a siRNA molecule or an antisense nucleic acid molecule. Preferably the agent selectively targets SEQ ID NO:6, foxp3 (SEQ ID NO:1) lacking exons 2 and 3, or a nucleic acid molecule comprising foxp3 exons 1 and 4 joined together.

The use of the foregoing compositions in the preparation of medicaments for treatment of disease, particularly cancer, also is provided in accordance with the invention.

These and other aspects of the invention, as well as various embodiments thereof, will become more apparent in reference to the drawings and detailed description of the invention.

BRIEF DESCRIPTION OF THE DRAWINGS

FIG. 11*a* demonstrates the presence of a band of the expected size for all three melanoma cell lines tested. To demonstrate the specificity of the reaction, the antibody was pre-blocked for 2 hours at room temperature with either the peptide used for immunization or an irrelevant peptide control (0.2 μg/ml). The antibody/peptide mixture was then used for Western blotting and band density was determined using ImageQuaNT software. This analysis is shown in FIG. 11*b*, and demonstrates that the band intensity is greatly reduced after blocking with the specific peptide.

DETAILED DESCRIPTION OF THE INVENTION

Figure 1:
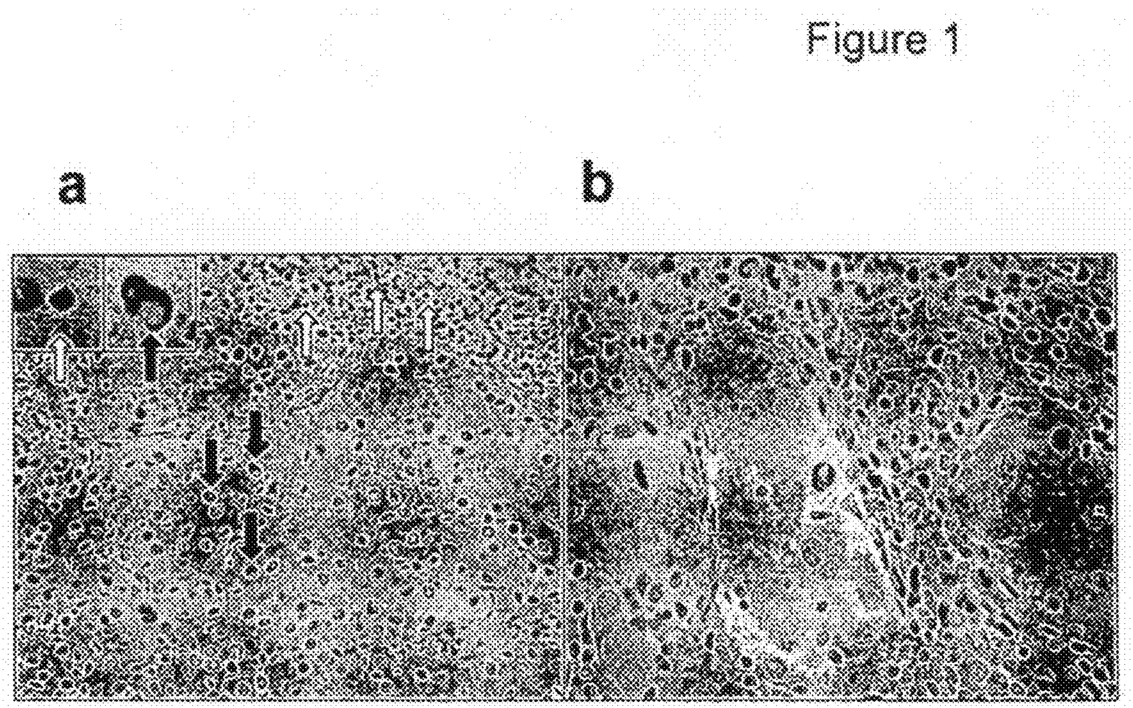
FIG. 1: FoxP3 expression by lymphocytes and tumor cells in metastatic melanoma tissue sections. (a); FoxP3 staining in cells with the morphology of lymphocytes (open arrows) or tumor cells (solid arrows) at 10× magnification. An enlarged (300%) view of each cell type is shown in the inset. (b); co-staining for FoxP3 (brown, nuclear) and Melan-A (pink, cytoplasmic) at 40× magnification.

The invention relates in part to the discovery that FoxP3 polypeptides and nucleic acid molecules that encode the FoxP3 polypeptides are expressed in cancer cells and tumors. As used herein, the "nucleic acid molecules that encode" means the nucleic acid molecules that code for the FoxP3 polypeptides or fragments thereof, particularly immunogenic fragments. These nucleic acid molecules may be DNA or may be RNA (e.g., mRNA). The FoxP3 nucleic acid molecules of the invention also encompass variants of the nucleic acid molecules described herein. These variants may be splice variants, some of which are described herein for FoxP3, or allelic variants of certain sequences provided. Variants of the nucleic acid molecules of the invention are intended to include homologs and alleles which are described further below. Further, as used herein, the term "FoxP3 molecules"

includes FoxP3 polypeptides and fragments thereof as well as FoxP3 nucleic acids and fragments (such as exon sequences). In all embodiments, human FoxP3 polypeptides and the nucleic acid molecules that encode them are preferred.

In one aspect, the invention provides isolated nucleic acid molecules that are splice variants of FoxP3 and may encode variant FoxP3 polypeptides. The isolated nucleic acid molecules of this aspect of the invention comprise: (a) nucleotide sequences set forth as or comprising SEQ ID NO:6 or FoxP3 (SEQ ID NO:1) lacking exons 2 and 3 or FoxP3 exons 1 and 4 joined together; (b) isolated nucleic acid molecules which hybridize under highly stringent conditions to the nucleic acid molecules of (a) and preferably which code for a FoxP3 polypeptide; (c) nucleic acid molecules that differ from (a) or (b) due to the degeneracy of the genetic code, and (d) full-length complements of (a), (b) or (c).

The novel FoxP3 splice variant is referred to herein primarily as Δ2,3. This nomenclature was developed on the basis of naming the first coding exon as exon 1. This is the convention commonly adopted within the FoxP3 literature, and as such, the splice variant detected in Treg is generally referred to as Δ2 (38-40). However, there is an additional exon upstream of the translation start site, and the Genbank entry for the FOXP3 gene refers to this as exon 1 (see accession number NM_014009). Accordingly, the first coding exon is referred to as exon 2. This alternative nomenclature has also been used in a recent publication (27). Therefore, the splice variant detected in tumor cells may be referred to as Δ2, 3 or Δ3,4 herein.

As used herein the term "isolated nucleic acid molecule" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein because it is readily manipulable by standard techniques known to those of ordinary skill in the art.

The FoxP3 nucleic acid molecules of the invention also encompass homologs and alleles which can be identified by conventional techniques. Identification of human and other organisms' homologs of FoxP3 polypeptides will be familiar to those of skill in the art. In general, nucleic acid hybridization is a suitable method for identification of homologous sequences of another species (e.g., human, cow, sheep, dog, rat, mouse), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the FoxP3 nucleic acid molecules identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of the FoxP3 nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, homologs and alleles typically will share at least 90% nucleotide identity and/or amino acid identity to the sequences of FoxP3 nucleic acids and polypeptides, respectively, in some instances will share at least 95% nucleotide identity and/or amino acid identity, in other instances will share at least 97% nucleotide identity and/or amino acid identity, in other instances will share at least 98% nucleotide identity and/or amino acid identity, and in other instances will share at least 99% nucleotide identity and/or amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using a number of sequence analysis software programs, such as the MacVector sequence analysis software (Accelrys Software Inc., San Diego, Calif.). Watson-Crick complements of the foregoing nucleic acids also are embraced by the invention.

In another aspect of the invention, nucleic acid molecules are provided which include unique fragments of the nucleotide sequences of the invention and complements thereof. The invention, in a preferred embodiment, provides unique fragments of SEQ ID NO:6 or FoxP3 exons 1 and 4 joined together and complements thereof. A unique fragment is one that is a 'signature' for the larger nucleic acid. It, for example, is long enough to assure that its precise sequence is not found in molecules outside of the nucleic acid molecules that encode the FoxP3 polypeptides defined above. Those of ordinary skill in the art may apply no more than routine procedures to determine if a fragment is unique within the human genome. In some instances the unique fragment is at least about 5, 6, 7, 8, 9, 10, 11, 12, 13, 14, 15, 16, 17, 18, 19, 20, 25, 30, 35, 40, 45, 50, 75, or 100 amino acids in length.

Unique fragments can be used as probes in Southern blot assays and microarray assays to identify such nucleic acid molecules, or can be used as probes in amplification assays such as those employing the polymerase chain reaction (PCR), including, but not limited to reverse transcribed (RT)-PCR and RT-real-time PCR. As known to those skilled in the art, large probes such as 200 nucleotides or more are preferred for certain uses such as Southern blots, while smaller fragments will be preferred for uses such as microarrays and PCR. Unique fragments also can be used to produce fusion proteins for generating antibodies or determining binding of the polypeptide fragments, or for generating immunoassay components. Likewise, unique fragments can be employed to produce nonfused fragments of the FoxP3 polypeptides useful, for example, in the preparation of antibodies and in immunoassays.

In screening for FoxP3 genes, a Southern blot may be performed using the foregoing conditions, together with a detectably labeled probe (e.g. radioactive or chemiluminescent probes). After washing the membrane to which the DNA is finally transferred, the membrane can be placed against X-ray film or analyzed using a phosphorimager device to detect the radioactive or chemiluminescent signal. In screening for the expression of FoxP3 nucleic acids, Northern blot hybridizations using the foregoing conditions or microarrays can be performed on samples taken from cancer patients or subjects suspected of having a condition characterized by abnormal cell proliferation or neoplasia. Amplification protocols such as polymerase chain reaction using primers that hybridize to the sequences presented also can be used for detection of the FoxP3 genes or expression thereof.

Identification of related sequences can also be achieved using polymerase chain reaction (PCR) and other amplification techniques suitable for cloning related nucleic acid sequences. Again, nucleic acids are preferably amplified from a tissue-specific library (e.g., testis, brain, cancer cells).

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating FoxP3 polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATI' (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1-20 nucleotides). In preferred embodiments, these modified nucleic acid molecules and/or the polypeptides they encode retain at least one activity or function of the unmodified nucleic acid molecule and/or the polypeptides, such as antigenicity, receptor binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on.

In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of activity or structural relation to the nucleic acids and/or polypeptides disclosed herein. As used herein the terms: “deletion”, “addition”, and “substitution” mean deletion, addition, and substitution changes to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleic acids of a sequence of the invention.

According to yet another aspect of the invention, an expression vector comprising any of the isolated nucleic acid molecules of the invention, preferably operably linked to a promoter is provided. In a related aspect, host cells transformed or transfected with such expression vectors also are provided. As used herein, a “vector” may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids, and virus genomes.

A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript.

Vectors may further contain one or more marker sequences suitable for use in the identification of cells which have or have not been transformed or transfected with the vector.

Markers include, for example, genes encoding proteins which increase or decrease either resistance or sensitivity to antibiotics or other compounds, genes which encode enzymes whose activities are detectable by standard assays known in the art, e.g., β-galactosidase or alkaline phosphatase, and genes which visibly affect the phenotype of transformed or transfected cells, hosts, colonies or plaques, e.g., green fluorescent protein. Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. As used herein, "operably joined" and "operably linked" are used interchangeably and should be construed to have the same meaning. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region is capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

It will also be recognized that the invention embraces the use of the FoxP3 nucleic acid molecules and genomic sequences in expression vectors, as well as to transfect host cells and cell lines, be these prokaryotic, e.g., *E. coli*, or eukaryotic, e.g., CHO cells, COS cells, yeast expression systems, and recombinant baculovirus expression in insect cells. Especially useful are mammalian cells such as human, mouse, hamster, pig, goat, primate, etc. They may be of a wide variety of tissue types, including mast cells, fibroblasts, oocytes, and lymphocytes, and may be primary cells and cell lines. Specific examples include dendritic cells, peripheral blood leukocytes, bone marrow stem cells and embryonic stem cells. The expression vectors require that the pertinent sequence, i.e., those nucleic acids described herein, be operably linked to a promoter.

The invention, in one aspect, also permits the construction of FoxP3 gene "knock-outs", "knockdowns" and "knock-ins" in cells and in animals, providing materials for studying certain aspects of cancer and immune system responses to cancer.

Expression vectors containing all the necessary elements for expression are commercially available and known to those skilled in the art. Cells are genetically engineered by the introduction into the cells of heterologous DNA or RNA encoding a FoxP3 polypeptide, a mutant FoxP3 polypeptide, fragments, or variants thereof. The heterologous DNA or RNA is placed under operable control of transcriptional elements to permit the expression of the heterologous DNA in the host cell.

Preferred systems for mRNA expression in mammalian cells are those such as pcDNA3.1 and pCDM8 (Invitrogen) that contain a selectable marker (which facilitates the selection of stably transfected cell lines) and contain the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element.

The invention also embraces kits termed expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also includes kits for amplification of a FoxP3 nucleic acid, including at least one pair of amplification primers which hybridize to a FoxP3 nucleic acid, preferably a FoxP3 nucleic acid in which exons 1 and 4 are joined, such as SEQ ID NO:6 or SEQ ID NO:1 lacking exons 2 and 3. The primers preferably are about 12, 13, 14, 15, 16, 17, 18, 19, 20, 21, 22, 23, 24, 25, 26, 27, 28, 29, 30, 31 or 32 nucleotides in length and are non-overlapping to prevent formation of "primer-dimers". One of the primers will hybridize to one strand of the FoxP3 nucleic acid and the second primer will hybridize to the complementary strand of the FoxP3 nucleic acid, in an arrangement that permits amplification of the FoxP3 nucleic acid. Selection of appropriate primer pairs is standard in the art. For example, the selection can be made with assistance of a computer program designed for such a purpose, optionally followed by testing the primers for amplification specificity and efficiency.

The invention, in another aspect provides isolated polypeptides (including whole proteins and partial proteins) encoded by the foregoing FoxP3 nucleic acids, such as SEQ ID NO:11 (Δ⅔ isoform polypeptide) and SEQ ID NO:12 (full-length polypeptide). The amino acids of the invention are also intended to encompass amino acid sequences that result from the translation of the nucleic acid sequences provided herein in a different reading frame.

Such polypeptides are useful, for example, alone or as fusion proteins to generate antibodies, and as components of an immunoassay or diagnostic assay. Immunogenic FoxP3 polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Fragments of the immunogenic FoxP3 polypeptides (including immunogenic peptides) also can be synthesized chemically using well-established methods of peptide synthesis. Thus, fragments of the disclosed polypeptides are useful for eliciting an immune response.

Fragments of a polypeptide preferably are those fragments that retain a distinct functional capability of the polypeptide. Functional capabilities that can be retained in a fragment of a polypeptide include interaction with antibodies or MHC molecules (e.g. immunogenic fragments), interaction with other polypeptides or fragments thereof, selective binding of nucleic acids or proteins, and enzymatic activity. One important activity is the ability to provoke in a subject an immune response. As will be recognized by those skilled in the art, the size of the fragment that can be used for inducing an immune response will depend upon factors such as whether the epitope recognized by an antibody is a linear epitope or a conformational epitope or the particular MHC molecule that binds to and presents the fragment (e.g. HLA class I or II). Thus, some immunogenic fragments of FoxP3 polypeptides will consist of longer segments while others will consist of shorter segments, (e.g., about 5, 6, 7, 8, 9, 10, 11 or 12 or more amino acids long, including each integer up to the full length of the FoxP3 polypeptide). Those skilled in the art are well versed in methods for selecting immunogenic fragments of polypeptides.

The invention embraces variants of the FoxP3 polypeptides described above. As used herein, a "variant" of a FoxP3 polypeptide is a polypeptide which contains one or more modifications to the primary amino acid sequence of a FoxP3 polypeptide. Modifications which create a FoxP3 polypeptide variant can be made to a FoxP3 polypeptide 1) to reduce or eliminate an activity of a FoxP3 polypeptide; 2) to enhance a property of a FoxP3 polypeptide, such as protein stability in an expression system or the stability of protein-protein binding; 3) to provide a novel activity or property to a FoxP3 polypeptide, such as addition of an antigenic epitope or addition of a detectable moiety; or 4) to provide equivalent or better binding to a MHC molecule.

Modifications to a FoxP3 polypeptide are typically made to the nucleic acid which encodes the FoxP3 polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the FoxP3 polypeptide amino acid sequence. One of skill in the art will be familiar with methods for predicting the effect on protein conformation of a change in protein sequence, and can thus "design" a variant FoxP3 polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a FoxP3 polypeptide can be proposed and tested to determine whether the variant retains a desired conformation.

In general, variants include FoxP3 polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a FoxP3 polypeptide by eliminating proteolysis by proteases in an expression system (e.g., dibasic amino acid residues in yeast expression systems in which KEX2 protease activity is present).

Mutations of a nucleic acid which encode a FoxP3 polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant FoxP3 polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a FoxP3 gene or cDNA clone to enhance expression of the polypeptide. The activity of variants of FoxP3 polypeptides can be tested by cloning the gene encoding the variant FoxP3 polypeptide into a bacterial or mammalian expression vector, introducing the vector into an appropriate host cell, expressing the variant FoxP3 polypeptide; and testing for a functional capability of the FoxP3 polypeptides, as will be known to one of ordinary skill in the art.

The skilled artisan will also realize that conservative amino acid substitutions may be made in immunogenic FoxP3 polypeptides to provide functionally equivalent variants, or homologs of the foregoing polypeptides, i.e., the variants retain the functional capabilities of the immunogenic FoxP3 polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants or homologs of the FoxP3 polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the FoxP3 polypeptides disclosed herein and retain the specific antibody-binding characteristics of the antigens.

Likewise, upon determining that a peptide derived from a FoxP3 polypeptide is presented by an MHC molecule and recognized by antibodies or T lymphocytes (e.g., helper T cells or CTLs), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.* 43:13-18, 1995; Drijfhout et al., *Human Immunol.* 43:1-12, 1995). The substituted peptides can then be tested for binding to the MHC molecule and recognition by antibodies or T lymphocytes when bound to MHC. These variants can be tested for improved stability and are useful, inter alia, in vaccine compositions.

Conservative amino-acid substitutions in the amino acid sequence of FoxP3 polypeptides to produce functionally equivalent variants of FoxP3 polypeptides typically are made by alteration of a nucleic acid encoding a FoxP3 polypeptide. Such substitutions can be made by a variety of methods known to one of ordinary skill in the art. For example, amino acid substitutions may be made by PCR-directed mutation, site-directed mutagenesis, or by chemical synthesis of a gene encoding a FoxP3 polypeptide. Where amino acid substitutions are made to a small unique fragment of a FoxP3 polypeptide, such as an antigenic epitope recognized by autologous or allogeneic sera or T lymphocytes, the substitutions can be made by directly synthesizing the peptide. The activity of functionally equivalent variants of FoxP3 polypeptides can be tested by cloning the gene encoding the altered FoxP3 polypeptide into a bacterial or mammalian expression vector, introducing the vector into an appropriate host cell, expressing the altered polypeptide, and testing for a functional capability of the FoxP3 polypeptides as disclosed herein. Peptides that are chemically synthesized can be tested directly for function, e.g., for binding to antisera recognizing associated antigens.

The invention as described herein has a number of uses, some of which are described elsewhere herein. In one aspect of the invention a method diagnosing cancer is provided, in which the expression of FoxP3 nucleic acids or polypeptides is indicative of and diagnostic for cancer. FoxP3 nucleic acids or polypeptides can be identified by obtaining a biological sample from a subject. In another aspect, methods for treating or preventing cancer are provided. Cancer can be treated by reducing the expression of FoxP3 nucleic acids or polypeptides.

As used herein, a "subject" is preferably a human, non-human primate, cow, horse, pig, sheep, goat, dog, cat or rodent. In all embodiments, human subjects are preferred. In some embodiments, the subject is suspected of having cancer or has been diagnosed with cancer. Cancers in which the FoxP3 nucleic acid or polypeptide are expressed include melanoma, bladder cancer, prostate cancer, breast cancer, colon cancer, lung cancer, glioblastoma and renal cell carcinoma.

As used herein, a biological sample includes, but is not limited to: tissue, cells, and/or body fluid (e.g., serum, blood, lymph node fluid, etc.). The fluid sample may include cells and/or fluid. The tissue and cells may be obtained from a subject or may be grown in culture (e.g., from a cell line). As used herein, a biological sample is body fluid, tissue or cells obtained from a subject using methods well-known to those of ordinary skill in the related medical arts. The biological sample can include tumor tissue or cells, normal tissue or cells, to or combinations thereof. In some embodiments, the biological sample is treated to remove T regulatory cells.

Thus determining the expression of FoxP3 polypeptides or nucleic acid molecules in a biological sample of a subject can be used to diagnose whether the subject has cancer.

Measurement of the expression of FoxP3 polypeptides or nucleic acid molecules over time by sequential determinations permits monitoring of the disease and/or the effects of a course of treatment. For example, a sample, such as serum, blood, or lymph node fluid, may be obtained from a subject, tested for expression of FoxP3 molecules, and at a second, subsequent time, another sample may be obtained from the subject and similarly tested. The results of the first and second (or subsequent) tests can be compared as a measure of the onset, regression or progression of cancer, or, if cancer treatment was undertaken during the interval between obtaining the samples, the effectiveness of the treatment may be evaluated by comparing the results of the two tests. Other methods will be apparent to one of skill in the art.

Diagnostic methods of the invention involve determining the expression of one or more of the FoxP3 polypeptides or the nucleic acid molecules that encode them, as described herein. Such determinations can be carried out via any standard nucleic acid assay, including the polymerase chain reaction or assaying with hybridization probes, which may be labeled, or by assaying biological samples with binding partners (e.g., antibodies) for FoxP3 polypeptides.

The diagnostic methods of the invention can be used to detect the presence of a disorder associated with aberrant expression of a FoxP3 molecule (e.g., onset of the disorder), as well as to assess the progression and/or regression of the disorder such as in response to treatment (e.g., chemotherapy, radiation). According to this aspect of the invention, the method for diagnosing a disorder characterized by aberrant expression of a FoxP3 molecule involve: detecting expression of a FoxP3 molecule in a first biological sample obtained from a subject, wherein differential expression of the FoxP3 molecule compared to a control sample indicates that the subject has a disorder characterized by aberrant expression of a FoxP3 molecule, such as cancer.

As described herein, FoxP3 molecules are expressed in testis tissue and certain other normal tissues (brain, fetal brain, $T_{reg}$ cells). Therefore, in all of the diagnostic methods described herein, the biological sample preferably does not contain testis, brain or $T_{reg}$ cells or tissue in order to avoid false-positive results.

As used herein, "aberrant expression" of a FoxP3 molecule is intended to include any expression that is statistically significant different from the expected (e.g., normal or baseline) amount of expression. For example, expression of a FoxP3 molecule (i.e., FoxP3 polypeptides or the nucleic acid molecules that encode them) in a tissue that is not expected to express the FoxP3 molecule would be included in the definition of "aberrant expression". Likewise, expression of the FoxP3 molecule that is determined to be expressed at a significantly higher or lower level than expected is also included. Therefore, a determination of the level of expression of one or more of the FoxP3 polypeptides and/or the nucleic acids that encode them is diagnostic of cancer if the level of expression is above a baseline level determined for that tissue type. The baseline level of expression can be determined using standard methods known to those of skill in the art. Such methods include, for example, assaying a number of histologically normal tissue samples (preferably not testis) from subjects that are clinically normal (i.e. do not have clinical signs of cancer in that tissue type) and determining the mean level of expression for the samples.

The level of expression of the nucleic acid molecules of the invention or the polypeptides they encode can indicate cancer in the tissue when the level of expression is significantly more in the tissue than in a control sample. In some embodiments, a level of expression in the tissues that is at least about 5%, 10%, 20%, 30%, 40%, 50%, 60%, 70%, 80%, 90%, 100%, 150%, 200%, 250%, 300%, 400%, or 500% more than the level of expression in the control tissue indicates cancer in the tissue.

As used herein the term "control" means predetermined values, and also means samples of materials tested in parallel with the experimental materials. Examples include samples from control populations, biopsy samples taken from tissue adjacent to a biopsy sample suspected of being cancerous and control samples generated through manufacture to be tested in parallel with the experimental samples.

As used herein the term "control" includes positive and negative controls which may be a predetermined value that can take a variety of forms. The control(s) can be a single cut-off value, such as a median or mean, or can be established based upon comparative groups, such as in groups having normal amounts of FoxP3 molecules of the invention and groups having abnormal amounts of FoxP3 molecules of the invention. Another example of a comparative group is a group having a particular disease, condition and/or symptoms and a group without the disease, condition and/or symptoms. Another comparative group is a group with a family history of a particular disease and a group without such a family history of the particular disease. The predetermined control value can be arranged, for example, where a tested population is divided equally (or unequally) into groups, such as a low-risk group, a medium-risk group and a high-risk group or into quadrants or quintiles, the lowest quadrant or quintile being individuals with the lowest risk or lowest expression levels of a FoxP3 molecule of the invention that is up-regulated in cancer and the highest quadrant or quintile being individuals with the highest risk or highest expression levels of a FoxP3 molecule of the invention that is up-regulated in cancer.

The predetermined value of a control will depend upon the particular population selected. For example, an apparently healthy population will have a different "normal" FoxP3 molecule expression level range than will a population which is known to have a condition characterized by aberrant expression of the FoxP3 molecule, e.g., cancer. Accordingly, the predetermined value selected may take into account the category in which an individual falls. Appropriate ranges and categories can be selected with no more than routine experimentation by those of ordinary skill in the art. Typically the control will be based on apparently healthy individuals in an appropriate age bracket. As used herein, the term "increased expression" means a higher level of expression relative to a selected control.

The invention involves in some aspects diagnosing or monitoring cancer by determining the level of expression of one or more FoxP3 nucleic acid molecules and/or determining the level of expression of one or more FoxP3 polypeptides they encode. In some important embodiments, this determination is performed by assaying a tissue sample from a subject for the level of expression of one or more FoxP3 nucleic acid molecules or for the level of expression of one or more FoxP3 polypeptides encoded by the nucleic acid molecules of the invention. Preferred FoxP3 nucleic acid molecules include those in which exons 1 and 4 are joined, such as nucleic acids that include SEQ ID NO:6 or SEQ ID NO:1 lacking exons 2 and 3.

The expression of the molecules of the invention may be determined using routine methods known to those of ordinary skill in the art. These methods include, but are not limited to: direct RNA amplification, reverse transcription of RNA to cDNA, real-time RT-PCR, amplification of cDNA, hybridization, and immunologically based assay methods, which include, but are not limited to immunohistochemistry, antibody sandwich capture assay, ELISA, and enzyme-linked immunospot assay (EliSpot assay). For example, the determination of the presence of level of nucleic acid molecules of the invention in a subject or tissue can be carried out via any standard nucleic acid determination assay, including the polymerase chain reaction, or assaying with labeled hybridization probes. Such hybridization methods include, but are not limited to microarray techniques.

These methods of determining the presence and/or level of the molecules of the invention in cells and tissues may include use of labels to monitor the presence of the molecules of the invention. Such labels may include, but are not limited to, radiolabels or chemiluminescent labels, which may be utilized to determine whether a molecule of the invention is expressed in a cell or tissue, and to determine the level of expression in the cell or tissue. For example, a fluorescently labeled or radiolabeled antibody that selectively binds to a polypeptide of the invention may be contacted with a tissue or cell to visualize the polypeptide in vitro or in vivo. These and other in vitro and in vivo imaging methods for determining the presence of the nucleic acid and polypeptide molecules of the invention are well known to those of ordinary skill in the art.

The invention also involves the use of agents such as polypeptides that bind to FoxP3 polypeptides. Such agents can be used in methods of the invention including the diagnosis and/or treatment of cancer. Such binding agents can be used, for example, in screening assays to detect the presence or absence of FoxP3 polypeptides and can be used in quantitative binding assays to determine levels of expression in biological samples and cells. Such agents also may be used to inhibit the native activity of the FoxP3 polypeptides, for example, by binding to such polypeptides.

According to this aspect, the binding polypeptides bind to an isolated nucleic acid or protein of the invention, including the novel splice variant (SEQ ID NO:6) and unique fragments thereof. Preferably, the binding polypeptides bind to a FoxP3 polypeptide, or a unique fragment thereof.

In preferred embodiments, the binding polypeptide is an antibody or antibody fragment, such as an Fab or $F(ab)_2$ fragment of an antibody. Typically, the fragment includes a CDR3 region that is selective for the FoxP3 polypeptide. Any of the various types of antibodies can be used for this purpose, including polyclonal antibodies, monoclonal antibodies, humanized antibodies, and chimeric antibodies.

Thus, the invention provides agents which bind to FoxP3 polypeptides encoded by FoxP3 nucleic acid molecules of the invention, and in certain embodiments preferably to unique fragments of the FoxP3 polypeptides. Such binding partners can be used in screening assays to detect the presence or absence of a FoxP3 polypeptide and in purification protocols to isolate such FoxP3 polypeptides. Likewise, such binding partners can be used to selectively target drugs, toxins or other molecules (including detectable diagnostic molecules) to cells which express FoxP3 polypeptides. In this manner, for example, cells present in solid or non-solid tumors which express FoxP3 polypeptides can be treated with cytotoxic compounds that are selective for the FoxP3 molecules (nucleic acids and/or antigens). Such binding agents also can be used to inhibit the native activity of the FoxP3 polypeptide, for example, to further characterize the functions of these molecules.

The antibodies of the present invention thus are prepared by any of a variety of methods, including administering a protein, fragments of a protein, cells expressing the protein or fragments thereof and the like to an animal to induce polyclonal antibodies. The present invention also provides methods of producing monoclonal antibodies to the FoxP3 molecules of the invention described herein. The production of monoclonal antibodies is performed according to techniques well known in the art. As detailed herein, such antibodies may be used for example to identify tissues expressing protein or to purify protein. Antibodies also may be coupled to specific labeling agents or imaging agents, including, but not limited to a molecule preferably selected from the group consisting of fluorescent, enzyme, radioactive, metallic, biotin, chemiluminescent, bioluminescent, chromophore, or colored, etc. In some aspects of the invention, a label may be a combination of the foregoing molecule types.

Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3): The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of “humanized” antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762, and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')2, Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies, domain antibodies and heavy chain antibodies (Ablynx Nev., Ghent, Belgium).

Thus, the invention involves polypeptides of numerous size and type that bind specifically to FoxP3 polypeptides. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties.

The FoxP3 polypeptides of the invention can be used to screen peptide libraries, including phage display libraries, to identify and select peptide binding partners of the FoxP3 molecules of the invention. Such molecules can be used, as described, for screening assays, for diagnostic assays, for purification protocols or for targeting drugs, toxins and/or labeling agents (e.g., radioisotopes, fluorescent molecules, etc.) to cells which express FoxP3 molecules such as cancer cells which have aberrant FoxP3 expression.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the FoxP3 polypeptide. This process can be repeated through several cycles of reselection of phage that bind to the FoxP3 polypeptide. Repeated rounds lead to enrichment of phage bearing particular sequences. DNA sequence analysis can be conducted to identify the sequences of the expressed polypeptides. The minimal linear portion of the sequence that binds to the FoxP3 polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the FoxP3 polypeptides.

As detailed herein, the foregoing antibodies and other binding molecules may be used to identify tissues with normal or aberrant expression of a FoxP3 polypeptide. Antibodies also may be coupled to specific diagnostic labeling agents for imaging of cells and tissues with normal or aberrant FoxP3 polypeptide expression or to therapeutically useful agents according to standard coupling procedures. As used herein, “therapeutically useful agents” include any therapeutic molecule which desirably is targeted selectively to a cell or tissue selectively with an aberrant FoxP3 expression.

Diagnostic agents for in vivo use include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99, iodine-131 and indium-111, and nuclides for nuclear magnetic resonance such as fluorine and gadolinium. Other diagnostic agents useful in the invention will be apparent to one of ordinary skill in the art.

The antibodies of the present invention can also be used to therapeutically target FoxP3 polypeptides. In one embodiment, antibodies can be used to target FoxP3 antigens expressed on the cell surface, such as FoxP3 peptides presented by MHC molecules. This can be accomplished, for example, by raising antibodies that recognize the complex of FoxP3 peptides and MHC molecules.

These antibodies can be linked not only to a detectable marker but also an antitumor agent or an immunomodulator. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope preferably is an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide may a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Further, the cytotoxic radionuclide may emit Auger and low energy electrons and include the isotopes $^{125}$I, $^{123}$I or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Other antineoplastic agents that may be conjugated to the antibodies of the present invention include dolastatins (U.S. Pat. Nos. 6,034,065 and 6,239,104) and derivatives thereof. Of particular interest is dolastatin 10 (dolavaline-valine-dolaisoleuine-dolaproine-dolaphenine) and the derivatives auristatin PHE (dolavaline-valine-dolaisoleuine-dolaproine-phenylalanine-methyl ester) (Pettit, G. R. et al., *Anticancer Drug Des.* 13(4):243-277, 1998; Woyke, T. et al., *Antimicrob. Agents Chemother.* 45(12):3580-3584, 2001), and aurastatin E and the like. Toxins that are less preferred in the compositions and methods of the invention include poisonous lectins, plant toxins such as ricin, abrin, modeccin, botulinum and diphtheria toxins. Of course, combinations of the various toxins could also be coupled to one antibody molecule thereby accommodating variable cytotoxicity. Other chemotherapeutic agents are known to those skilled in the art.

Agents that act on the tumor vasculature can include tubulin-binding agents such as combrestatin A4 (Griggs et al., *Lancet Oncol.* 2:82, 2001), angiostatin and endostatin (reviewed in Rosen, *Oncologist* 5:20, 2000, incorporated by reference herein) and interferon inducible protein 10 (U.S. Pat. No. 5,994,292). A number of antiangiogenic agents currently in clinical trials are also contemplated. Agents currently in clinical trials include: 2ME2, Angiostatin, Angiozyme, Anti-VEGF RhuMAb, Apra (CT-2584), Avicine, Benefin, BMS275291, Carboxyamidotriazole, CC4047, CC5013, CC7085, CDC801, CGP-41251 (PKC 412), CM101, Combretastatin A-4 Prodrug, EMD 121974, Endostatin, Flavopiridol, Genistein (GCP), Green Tea Extract, IM-862, ImmTher, Interferon alpha, Interleukin-12, Iressa (ZD1839), Marimastat, Metastat (Col-3), Neovastat, Octreotide, Paclitaxel, Penicillamine, Photofrin, Photopoint, PI-88, Prinomastat (AG-3340), PTK787 (ZK22584), RO317453, Solimastat, Squalamine, SU 101, SU 5416, SU-6668, Suradista (FCE 26644), Suramin (Metaret), Tetrathiomolybdate, Thalidomide, TNP-470 and Vitaxin. additional antiangiogenic agents are described by Kerbel, J. Clin. Oncol. 19(18s):45s-51s, 2001, which is incorporated by reference herein. Immunomodulators suitable for conjugation to the antibodies include α-interferon, γ-interferon, and tumor necrosis factor alpha (TNFα).

The coupling of one or more toxin molecules to the antibody is envisioned to include many chemical mechanisms, for instance covalent binding, affinity binding, intercalation, coordinate binding, and complexation. The toxic compounds used to prepare the immunotoxins are attached to the antibodies or antigen-binding fragments thereof by standard protocols known in the art.

In other aspects of the invention, the FoxP3 molecules and the antibodies and other binding molecules, as described herein, can be used for the treatment or prevention of disorders. When "disorder" is used herein, it refers to any pathological condition where the FoxP3 polypeptides are aberrantly expressed. An example of such a disorder is cancer, particularly melanoma, bladder cancer, prostate cancer, breast cancer, colon cancer, lung cancer, glioblastoma and renal cell carcinoma. In another aspect or the invention, such molecules can be used to inhibit immunological tolerance of tumors, by inhibiting the mechanism by which FoxP3 contributes to tolerance.

Conventional treatment for cancer may include, but is not limited to: surgical intervention, chemotherapy, radiotherapy, and adjuvant systemic therapies. In one aspect of the invention, treatment may include administering binding polypeptides such as antibodies that specifically bind to the FoxP3 polypeptide. These binding polypeptides can be optionally linked to one or more detectable markers, antitumor agents or immunomodulators as described above.

Cancer treatment or prevention, in another aspect of the invention, includes administering antisense molecules or molecules that produce RNA interference (RNAi) to reduce the expression level of FoxP3 nucleic acids or polypeptides and/or function level of FoxP3 polypeptides of the invention in the subject in cancers where a FoxP3 molecule is up-regulated. The use of RNAi involves the use of double-stranded RNA (dsRNA) to block gene expression (see: Sui, G, et al, Proc Natl. Acad. Sci. U.S.A. 99:5515-5520, 2002). Methods of applying RNAi strategies in embodiments of the invention are known and understood by one of ordinary skill in the art.

Methods in which small interfering RNA (siRNA) molecules are used to reduce the expression of FoxP3 may be used. In one aspect, a cell is contacted with a siRNA molecule to produce RNA interference (RNAi) that reduces expression of FoxP3. The siRNA molecule is directed against nucleic acids coding for FoxP3 (e.g. RNA transcripts including untranslated and translated regions). In a preferred aspect of the invention the siRNA is targeted to a FoxP3 splice variant in which exons 1 and 4 are joined, e.g., splice variants including SEQ ID NO:6. The expression level of the targeted FoxP3 molecules can be determined using well known methods such as FACS or Western blotting for determining the level of protein expression and Northern blotting or RT-PCR for determining the level of mRNA transcript of the FoxP3 gene.

As used herein, a "siRNA molecule" is a double stranded RNA molecule (dsRNA) consisting of a sense and an antisense strand or a single stranded molecule that has a dsRNA component, for example a section of the molecule that hybridizes to itself (e.g., a "hairpin" structure). The antisense strand of the siRNA molecule is a complement of the sense strand (Tuschl, T. et al., 1999, Genes & Dev., 13:3191-3197; Elbashir, S. M. et al., 2001, EMBO J., 20:6877-6888; incorporated herein by reference). In one embodiment the last nucleotide at the 3' end of the antisense strand may be any nucleotide and is not required to be complementary to the region of the target gene. The siRNA molecule may be 19-23 nucleotides in length and form a hairpin structure. In one preferred embodiment the siRNA molecule includes a two nucleotide 3' overhang on the sense strand. In a second preferred embodiment the two nucleotide overhang is thymidine-thymidine (TT). The siRNA molecule corresponds to at least a portion of the FoxP3 gene, preferably the novel FoxP3 splice variant described herein. In one embodiment the siRNA molecule corresponds to a region selected from a cDNA target gene beginning between 50 to 100 nucleotides downstream of the start codon. In a preferred embodiment the first nucleotide of the siRNA molecule is a purine.

The siRNA molecules can be plasmid-based. In a preferred method, a FoxP3 nucleic acid sequence is amplified using the well known technique of polymerase chain reaction (PCR). The use of the entire polypeptide encoding sequence is not necessary; as is well known in the art, a portion of the polypeptide encoding sequence is sufficient for RNA interference. The PCR fragment is inserted into a vector using routine techniques well known to those of skill in the art. Combinations of FoxP3 siRNA molecules can be expressed from a single vector or from multiple vectors introduced into cells.

In one aspect of the invention a mammalian vector comprising FoxP3 coding sequence is provided. The mammalian vectors include but are not limited to the pSUPER RNAi vectors (Brummelkamp, T. R. et al., 2002, Science, 296:550-553, incorporated herein by reference). In one embodiment a nucleotide coding sequence can be inserted into the mammalian vector using restriction sites, creating a stem-loop structure. In a second embodiment, the mammalian vector may comprise the polymerase-III H1-RNA gene promoter. The polymerase-III H1-RNA promoter produces a RNA transcript lacking a polyadenosine tail and has a well-defined start of transcription and a termination signal consisting of five thymidines (T5) in a row. The cleavage of the transcript at the termination site occurs after the second uridine and yields a transcript resembling the ends of synthetic siRNAs containing two 3' overhanging T or U nucleotides. The antisense strand of the siRNA molecule hybridizes to the corresponding region of the mRNA of the target gene.

Preferred systems for mRNA expression in mammalian cells are those such as pSUPER RNAi system as described in Brummelkamp et al. (2002, Science, 296:550-553). Other examples include but are not limited to pSUPER.neo, pSUPER.neo+gfp, pSUPER.puro, BLOCK-iT T7-TOPO linker, pcDNA1.2/V5-GW/lacZ, pENTR/U6, pLenti6-GW/U6-laminshrna, and pLenti6/BLOCK-iT-DEST. These vectors are available from suppliers such as Invitrogen, and one of skill in the art would be able to obtain and use them.

The invention includes kits for assaying the expression of FoxP3. An example of a kit may include an antibody or antigen-binding fragment thereof, that binds specifically to a FoxP3 polypeptide. The antibody, or antigen-binding fragment thereof, may be applied to a tissue or cell sample from a patient with cancer or suspected of having cancer and the sample then processed to assess whether specific binding occurs between the antibody and an antigen or other component of the sample. In addition, the antibody, or antigen-binding fragment thereof, may be applied to a body fluid sample, such as serum, from a subject, either suspected of having cancer, diagnosed with cancer, or believed to be free of cancer. As will be understood by one of skill in the art, such binding assays may also be performed with a sample or object contacted with an antibody and/or FoxP3 polypeptide that is in solution, for example in a 96-well plate, or applied directly to a solid support (i.e., an object's surface).

Another example of a kit of the invention is a kit that provides components necessary to determine the level of expression of one or more FoxP3 nucleic acid molecules of the invention. Such components may include primers useful for amplification of one or more FoxP3 nucleic acid molecules and/or other chemicals for PCR amplification. Another example of a kit of the invention is a kit that provides components necessary to determine the level of expression of one or more FoxP3 nucleic acid molecules of the invention using a method of hybridization.

The foregoing kits can include instructions or other printed material on how to use the various components of the kits for diagnostic purposes.

The invention further includes nucleic acid or protein microarrays (including antibody arrays) for the analysis of expression of FoxP3 polypeptides or nucleic acids encoding such antigens. In this aspect of the invention, standard techniques of microarray technology are utilized to assess expression of the FoxP3 polypeptides and/or identify biological constituents that bind such antigens. The constituents of biological samples include antibodies, lymphocytes (particularly T lymphocytes), and the like. Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezoelectric delivery. Probes may be covalently linked to the substrate. Nucleic acid probes preferably are linked using UV irradiation or heat.

Protein microarray technology, which is also known by other names including protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485):1760-1763, 2000.

Targets are peptides or proteins and may be natural or synthetic. The tissue may be obtained from a subject or may be grown in culture (e.g. from a cell line).

In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

Nucleic acid arrays, particularly arrays that bind FoxP3 nucleic acid sequences, also can be used for diagnostic applications, such as for identifying subjects that have a condition characterized by aberrant FoxP3 molecule expression, e.g., cancer. Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast, Nature Genetics*, Vol. 21, January 1999, the entire contents of which is incorporated by reference herein.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

According to a further aspect of the invention, compositions containing the FoxP3 nucleic acid molecules, siRNA molecules, antisense oligonucleotides, proteins, and binding polypeptides of the invention are provided. The compositions contain any of the foregoing therapeutic agents in a carrier, optionally a pharmaceutically acceptable carrier. Thus, in a related aspect, the invention provides a method for forming a medicament that involves placing a therapeutically effective amount of the therapeutic agent in the pharmaceutically acceptable carrier to form one or more doses. The effectiveness of treatment or prevention methods of the invention can be determined using standard diagnostic methods described herein.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term “pharmaceutically acceptable” means a non-toxic material that does not interfere with the effectiveness of the biological activity of the active ingredients. The term “physiologically acceptable” refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term “carrier” denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The therapeutics of the invention can be administered by any conventional route, including injection or by gradual infusion over time. The administration may, for example, be oral, intravenous, intratumoral, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, “Aerosols,” in Remington’s Pharmaceutical Sciences, 18th edition, 1990, pp 1694-1712). Those of skill in the art can readily determine the various parameters and conditions for producing antibody aerosols without undue experimentation. When using antisense preparations of the invention, slow intravenous administration is preferred.

The compositions of the invention are administered in effective amounts. An “effective amount” is that amount of a FoxP3 nucleic acid composition (preferably siRNA or antisense oligonucleotides) that alone, or together with further doses, produces the desired response, e.g., a reduction of expression of FoxP3 nucleic acids or polypeptide. In the case of treating a particular disease or condition characterized by expression of one or more FoxP3 polypeptides, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of FoxP3 nucleic acid (e.g., siRNA or antisense oligonucleotide) for producing the desired response in a unit of weight or volume suitable for administration to a patient. The response can, for example, be measured by determining FoxP3 expression following administration of the FoxP3 composition by measuring the expression of FoxP3, or by observing the physiological effects of the FoxP3 composition, such as regression of a tumor or decrease of disease symptoms. Other assays will be known to one of ordinary skill in the art and can be employed for measuring the level of the response.

The present invention therefore provides pharmaceutical compositions comprising an agent that reduces FoxP3 nucleic acid or polypeptide expression. These pharmaceutical compositions may be administered orally, rectally, parenterally, intratumorally, intrathecally, intracistemally, intravaginally, intraperitoneally, topically (as by powders, ointments, drops or transdermal patch), bucally, or as an oral or nasal spray. As used herein, "pharmaceutically acceptable carrier" is intended to mean a non-toxic solid, semisolid or liquid filler, diluent, encapsulating material or formulation auxiliary of any type. The term "parenteral" as used herein refers to modes of administration which include intravenous, intramuscular, intrathecal, intraperitoneal, infrasternal, subcutaneous and intraarticular injection and infusion.

When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712). Those of skill in the art can readily determine the various parameters and conditions for producing antibody aerosols without undue experimentation.

Where FoxP3 polypeptides are used for vaccination, modes of administration which effectively deliver the FoxP3 polypeptide and adjuvant, such that an immune response to the polypeptide is increased, can be used. For administration of a FoxP3 polypeptide in adjuvant, preferred methods include intradermal, intravenous, intramuscular and subcutaneous administration. Although these are preferred embodiments, the invention is not limited by the particular modes of administration disclosed herein. Standard references in the art (e.g., Remington's Pharmaceutical Sciences, 18th edition, 1990) provide modes of administration and formulations for delivery of immunogens with adjuvant or in a non-adjuvant carrier.

One of ordinary skill will recognize that the choice of a particular mode of administration can be made empirically based upon considerations such as the particular disease state being treated; the type and degree of the response to be achieved; the specific agent or composition employed; the age, body weight, general health, sex and diet of the patient; the time of administration and rate of excretion of the agent or composition; the duration of the treatment; drugs (such as a chemotherapeutic agent or other cancer therapeutic) used in combination or coincidental with the specific composition; and like factors well known in the medical arts.

Pharmaceutical compositions of the present invention for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Illustrative examples of suitable aqueous and nonaqueous carriers, diluents, solvents or vehicles include, but are not limited to, water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being comingled with the molecules of the present invention, and with each other, in a manner such that there is no interaction which would substantially impair the desired pharmaceutical efficacy.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, parabens, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the therapeutic agent or inhibitor, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacteria-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are preferably mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents as appropriate.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Illustrative examples of embedding compositions which can be used include polymeric substances and waxes.

Liquid dosage forms for oral administration include, but are not limited to, pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions may also contain adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The agent or inhibitor can also be administered in the form of liposomes. As is known to those skilled in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the agent or inhibitor, stabilizers, preservatives, excipients, and the like. Preferred lipids are phospholipids and phosphatidyl cholines (lecithins), both natural and synthetic. Methods to form liposomes are known in the art. See, e.g., Prescott, ed., METHODS IN CELL BIOLOGY, Volume XIV, Academic Press, New York, N.Y. (1976), p. 33 et seq.

The agents of the present invention can be formulated according to known methods to prepare pharmaceutically acceptable compositions, whereby these materials, or their functional derivatives, are combined in a mixture with a pharmaceutically acceptable carrier vehicle. Suitable vehicles and their formulation, inclusive of other human proteins, e.g., human serum albumin, are well known in the art. In order to form a pharmaceutically acceptable composition suitable for effective administration, such compositions will contain an effective amount of one or more agents of the present invention.

Additional pharmaceutical methods may be employed to control the duration of action. Controlled release preparations may be achieved through the use of polymers to complex or absorb the therapeutic agents of the invention. The controlled delivery may be exercised by selecting appropriate macromolecules (such as polyesters, polyamino acids, polyvinyl, pyrrolidone, ethylenevinylacetate, methylcellulose, carboxymethylcellulose, or protamine sulfate) and methods of incorporation in order to control release. Another possible method to control the duration of action by controlled release preparations is to incorporate antibodies into particles of a polymeric material such as polyesters, polyamino acids, hydrogels, poly(lactic acid) or ethylene vinyl acetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly (methylmethacylate) microcapsules, respectively, or in colloidal drug delivery systems, for example, liposomes, albumin microspheres, microemulsions, nanoparticles, and nanocapsules or in macroemulsions.

The pharmaceutical formulations of the present invention are prepared, for example, by admixing the active agent with solvents and/or carriers, optionally using emulsifiers and/or dispersants, while if water is used as the diluent, organic solvents may be used as solubilizing agents or auxiliary solvents. As described above, the excipients used include, for example, water, pharmaceutically acceptable organic solvents such as paraffins, vegetable oils, mono- or polyfunctional alcohols, carriers such as natural mineral powders, synthetic mineral powders, sugars, emulsifiers and lubricants.

One of ordinary skill will appreciate that effective amounts of the inventive therapeutic agents can be determined empirically and may be employed in pure form or, where such forms exist, in pharmaceutically acceptable salt, ester or prodrug form. The agonist or antagonist my be administered in compositions in combination with one or more pharmaceutically acceptable excipients. It will be understood that, when administered to a human patient, the total daily usage of the agents and compositions of the present invention will be decided by the attending physician within the scope of sound medical judgement. The specific therapeutically effective dose level for any particular patient will depend upon a variety of factors including the type and degree of the response to be achieved; the specific agent or composition employed; the age, body weight, general health, sex and diet of the patient; the time of administration, route of administration, and rate of excretion of the agent or composition; the duration of the treatment; drugs (such as a chemotherapeutic agent) used in combination or coincidental with the specific composition; and like factors well known in the medical arts.

Techniques of dosage determination are well known in the art for antibody and peptide agents. In general, it is desirable to provide a patient with a dosage of antibody or peptide agent in the range of from about 1 pg/kg to 10 mg/kg (body weight of patient). The therapeutically effective dose can be lowered if the agent of the present invention is additionally administered with another compound. As used herein, one compound is said to be additionally administered with a second compound when the administration of the two compounds is in such proximity of time that both compounds can be detected at the same time in the patient's serum.

For example, satisfactory results are obtained by oral administration of therapeutic dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging may also be arranged in a patient specific manner to provide a predetermined concentration of an agent in the blood. Thus patient dosaging may be adjusted to achieve regular on-going trough blood levels, on the order of from 50 to 1000 ng/ml, preferably 150 to 500 ng/ml.

The agents of the present invention are intended to be provided to a patient in an amount sufficient to reduce the amount of expression of FoxP3 nucleic acid and/or polypeptide, i.e., an effective amount. An amount is said to be sufficient to "reduce the amount of expression of FoxP3 nucleic acid and/or polypeptide" if the dosage, route of administration, etc. of the agent is sufficient to reduce the amount of expression of FoxP3 nucleic acid and/or polypeptide as detected by any methodology known to persons skilled in the art, particularly those described herein.

In the case of treating a particular cancer, the desired response is inhibiting the progression of the cancer. This may involve only slowing the progression of the cancer temporarily, although more preferably, it involves halting the progression of the cancer permanently. This can be monitored by routine methods or can be monitored according to diagnostic methods of the invention discussed herein. The desired response to treatment of the disease or condition also can be delaying the onset or even preventing the onset of the disease or condition. Such an effect can be assayed, for example, by examining the onset of cancer symptoms occurring in vivo, determining proliferation or tumorigenicity of cancer cells (e.g., in animal tumor explant models), or by correlating in vitro blocking studies with predicted in vivo efficacy.

The agents that reduce the amount of expression of FoxP3 nucleic acid and/or polypeptide can be administered in combination with a vaccine targeted against FoxP3 and/or cancer-testis (CT) antigens, which are well know to the person skilled in the art. Thus the invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen.

Generally accepted animal models can be used for testing of immunization against cancer using one or more CT antigens. For example, human cancer cells can be introduced into a mouse to create a tumor, and FoxP3 and one or more CT antigens, such as NY-ESO-1, or nucleic acids encoding these can be delivered by the methods described herein. The effect on the cancer cells (e.g., reduction of tumor size) can be assessed as a measure of the effectiveness of the combination therapy. Of course, testing of the foregoing animal model using more conventional methods for immunization can include the administration of one or more CT antigen polypeptides or fragments derived therefrom, optionally combined with one or more adjuvants and/or cytokines to boost the immune response.

Methods for immunization, including formulation of a vaccine composition and selection of doses, route of administration and the schedule of administration (e.g. primary and one or more booster doses), are well known in the art.

As part of the immunization compositions, one or more antigens or immunogenic fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham), ISCOMATRIX® (CSL Ltd., Parkville, Victoria, Australia) derived from the bark of the *Quillaia saponaria* molina tree; QS-7, QS-17, QS-18, and QS-L1 (So et al., Mol. Cells. 7:178-186, 1997); incomplete Freund's adjuvant; complete Freund's adjuvant; montanide; alum; CpG oligonucleotides (see e.g. Kreig et al., Nature 374:546-9, 1995; U.S. Pat. No. 6,207,646) and other immunostimulatory oligonucleotides; various water-in-oil emulsions prepared from biodegradable oils such as squalene and/or tocopherol; and factors that are taken up by the so-called 'toll-like receptor 7' on certain immune cells that are found in the outside part of the skin, such as imiquimod (3M, St. Paul, Minn.). Preferably, the antigens are administered mixed with a combination of DQS21/MPL or ISCOMATRIX®. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g. Goding, Monoclonal Antibodies: Principles and Practice, 2nd Ed., 1986). Methods for the preparation of mixtures or emulsions of polypeptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., Science 268: 1432-1434, 1995), GM-CSF, IL-18 and IL-15 (Klebanoff et al. Proc. Natl. Acad. Sci. USA 2004 101:1969-74). Thus cytokines can be administered in conjunction with antigens and adjuvants to increase the immune response to the antigens.

There are a number of immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng P., et al. Proc. Natl. Acad. Sci. USA 95 (11):6284-6289 (1998)).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., J. Immunol, 154:5637-5648 (1995)). Tumor cell transfection with B7 has been discussed in relation to in vitro CTL expansion for adoptive transfer immunotherapy by Wang et al., (J. Immunol., 19:1-8 (1986)). Other delivery mechanisms for the B7 molecule include nucleic acid (naked DNA) immunization (Kim J., et al. Nat. Biotechnol., 15:7: 641-646 (1997)) and recombinant viruses such as adeno and pox (Wendtner et al., Gene Ther., 4:7:726-735 (1997)). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., Nature 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., J. Immunol., 158:637-642 (1997), Fenton et al., J. Immunother., 21:2:95-108 (1998)).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., J. Immunother., 21:2:95-108 (1998)). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., Nature, 393:474 (1998), Bennett et al., Nature, 393:478 (1998), Schoenberger et al., Nature, 393:480 (1998)). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor antigens which are normally encountered outside of an inflammatory context or are presented by non-professional APCs (tumor cells). In these situations Th help and B7 costimulation signals are not provided.

The invention contemplates delivery of nucleic acids, polypeptides or fragments thereof for vaccination. Delivery of polypeptides and fragments thereof can be accomplished according to standard vaccination protocols which are well known in the art. In another embodiment, the delivery of nucleic acid is accomplished by ex vivo methods, i.e. by removing a cell from a subject, genetically engineering the cell to include one or more CT antigens, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

A virus vector for delivering a nucleic acid encoding one or more CT antigens is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., Virology 219:220-227, 1996; Eloit et al., J. Virol. 7:5375-5381, 1997; Chengalvala et al., Vaccine 15:335-339, 1997), a modified retrovirus (Townsend et al., J. Virol. 71:3365-3374, 1997), a nonreplicating retrovirus (Irwin et al., J. Virol. 68:5036-5044, 1994), a replication defective Semliki Forest virus (Zhao et al., Proc. Natl. Acad. Sci. USA 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venzuelan equine encephalitis virus (Davis et al., J. Virol. 70:3781-3787, 1996), Sindbis virus (Pugachev et al., Virology 212:587-594, 1995), and Ty virus-like particle (Allsopp et al., Eur. J. Immunol. 26:1951-1959, 1996). A preferred virus vector is an adenovirus.

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids into cells, depending on whether the nucleic acids are introduced in vitro or in vivo in a host. Such techniques include transfection of nucleic acid-$CaPO_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a cancer-testis antigen, alone or as a complex with a MHC molecule. Especially preferred are monoclonal antibodies. Where liposomes are employed to deliver the nucleic acids, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like.

Polymeric delivery systems also have been used successfully to deliver nucleic acids into cells, as is known by those skilled in the art. Such systems even permit oral delivery of nucleic acids.

The administration of the agents of the present invention may be for either prophylactic or therapeutic purpose. When provided prophylactically, the agent is provided in advance of any cancer symptoms. The prophylactic administration of the agent serves to prevent or reduce the rate of onset of symptoms. When provided therapeutically, the agent is provided at (or after) the onset of the appearance of symptoms of actual disease. The therapeutic administration of the agent serves to reduce the severity and duration of cancer.

As described herein, reducing expression of FoxP3 nucleic acid and/or polypeptide can be used for treatment of cancer. For human cancers, particular examples include, biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma, neurosarcoma, chondrosarcoma, Ewing sarcoma, malignant fibrous histocytoma, glioma, esophageal cancer, hepatoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; testicular cancer; thyroid cancer including thyroid adenocarcinoma and medullar carcinoma; transitional cancer and renal cancer including adenocarcinoma and Wilms tumor.

The treatments described herein can be combined with conventional cancer treatments. Conventional treatment for cancer may include, but is not limited to: surgical intervention, chemotherapy, radiotherapy, and adjuvant systemic therapies. In one aspect of the invention, treatment may include administering binding polypeptides such as antibodies that specifically bind to the one or more CT antigens. These binding polypeptides can be optionally linked to one or more detectable markers, antitumor agents or immunomodulators as described herein and/or known in the art.

The pharmaceutical agents of the invention may be administered alone, in combination with each other, and/or in combination with other anti-cancer drug therapies and/or treatments. These therapies and/or treatments may include, but are not limited to: surgical intervention, chemotherapy, radiotherapy, and adjuvant systemic therapies.

The invention also provides a pharmaceutical kit comprising one or more containers comprising one or more of the pharmaceutical compounds or agents of the invention. Additional materials may be included in any or all kits of the invention, and such materials may include, but are not limited to buffers, water, enzymes, tubes, control molecules, etc. The kit may also include instructions for the use of the one or more pharmaceutical compounds or agents of the invention for the treatment of cancer.

The present invention is described in further detail in the following non-limiting examples.

EXAMPLES

Materials and Methods

Cells, Tissue and Media

Complete medium (RF-10) consisted of RPMI supplemented with 2 mM Glutamax, 100 U/ml penicillin, 100 μg/ml streptomycin and 10 mM HEPES (all from Invitrogen, Carlsbad, Calif.) and 10% FCS (fetal calf serum, Thermo Trace, Melbourne, VIC, Australia). Tumor cell lines and primary fibroblast cultures (derived from normal human dermis or foreskin tissue) were maintained in RF-10 and passaged when required using trypsin/EDTA (Invitrogen) or 2 mM EDTA in PBS, pH 7.4. Normal epidermal melanocyte cultures were obtained from Lonza Biosciences (Basel, Switzerland).

Melanoma tissue collected following surgical resection was formalin-fixed and embedded in paraffin for immunohistochemistry, or used to generate single cell suspensions as follows: tissue was finely chopped using a scalpel, gently homogenized to generate a single cell suspension and remaining fragments and clumps of cells removed by filtering. The cells were resuspended in FCS containing 10% DMSO (Sigma-Aldrich, Castle Hill, NSW, Australia) and cryopreserved in liquid nitrogen until required. The collection of tissue for these studies was approved by the Human Research and Ethics Committee (Austin Health, Melbourne, Australia), and all patients gave informed consent.

Peripheral blood mononuclear cells (PBMC) from buffy coats of healthy donors (Red Cross Blood Bank, Melbourne, Australia) were prepared by Ficoll-Paque density gradient centrifugation (Amersham Biosciences, Uppsala, Sweden). NK cells, monocytes and $CD4^+$ T cells were purified using the NK Cell isolation kit or CD14 or CD4 Microbeads, respectively, according to the manufacturer's recommendations (Miltenyi Biotec, Bergisch Gladbach, Germany). Cell purity was greater than 96% as determined by flow cytometry. Monocyte-derived dendritic cells (moDC) were generated by plating monocytes at $5\times10^5$ cells/ml in RF-10 supplemented with GM-CSF plus IL-4 for 6-7 days. The Treg cell line was generated following purification of $CD25^{hi}$ T cells from a disaggregated tumor sample using CD3 microbeads (Miltenyi) followed by CD25 Dynabeads (Invitrogen). The cells were expanded using 1 μg/ml PHA and feeder cells in RF-10 containing 150 IU/ml IL-2.

Immunohistochemistry

Immunohistochemistry was performed on formalin-fixed paraffin sections after EDTA buffer pH 8.0 (NeoMarkers, Fremont, Calif.) retrieval, as described (41). All sections were incubated with 3% $H_2O_2$/PBS for 10 minutes to block endogenous peroxidase. Rabbit polyclonal anti-FoxP3 antibody (Abeam, Cambridge, UK) was used at a 1:500 dilution for 1 hour. Dako Envision+™ polymer (DakoCytomation, Carpinteria, Calif.) was used as the secondary reagent and 3-amino-9-ethyl-carbazole (Sigma-Aldrich, St. Louis, Mo.) was used as the chromogen. All incubations were performed at room temperature using the Shandon Sequenza® immunostainer (Thermo Scientific, Waltham, Mass.). Slides were counterstained with Mayer's haematoxylin (Amber Scientific, Belmont, Wash.). Application of CrystalMount (Biomeda Corp., CA) preceded dehydration and mounting in DePeX (BDH 36125). Tonsil was used as a positive control for each run and a rabbit IgG (Vecta Laboratories, Burlingame, USA) negative control was included with every immunohistochemical test. Monoclonal antibody to Melan-A (clone A103) was produced at the Biological Production Facility, Ludwig Institute of Cancer Research.

Flow Cytometry and Cell Sorting

Fluorochrome-conjugated antibodies to human CD4 (clone UCHT2), CD19 (clone HIB19), CD31 (clone WM59), CD90 (clone 5E10) and isotype-matched control antibodies were from BD Biosciences (Franklin Lakes, N.J.). Anti-CD3 (clone S4.1) was from Invitrogen, anti-MCSP (clone EP-1) was from Miltenyi and anti-FoxP3 (clone 236A/E7) was from eBioscience (San Diego, Calif.). Staining of surface antigens was performed in 96-well plates by incubating the cells with an appropriate concentration of antibody (as determined by titration) in FACS buffer (PBS+2% FCS+0.04% sodium azide) for 15 minutes at 4° C. FoxP3 staining was performed after staining of surface antigens, using the FoxP3 Buffer Set from eBioscience according to the manufacturer's recommendations (with small modifications in reagent volume to allow staining in 96-well plates). Flow cytometric analysis was performed on a FACSCalibur or FACSCanto II instrument (BD), and data was analyzed using FlowJo (TreeStar Inc., Ashland, Oreg.). Mean fluorescence intensity (MFI) ratios were calculated by dividing the geometric mean channel fluorescence value of FoxP3 stained cells by that of isotype-matched control stained cells. Cell sorting was performed on a FACSAria instrument (BD Biosciences).

Epstein-Barr Virus (EBV)-Mediated Transformation of B Cells

Supernatant was collected following 5 days' culture of the lymphoblastoid marmoset cell line B95-8 latently infected with EBV. Virus-containing supernatant was 0.45 μm-filtered and diluted 1/10 with fresh RF-10 containing 1 μg/ml cyclosporine (Novartis Pharmaceuticals Australia, North Ryde, NSW, Australia). PBMC ($2\times10^6$ cells/ml) were cultured in this medium for 30 days, changing half of the medium weekly with fresh RF-10 containing cyclosporine.

T Cell Suppression Assay $CD8^+$ T cells were purified from PBMC using CD8 microbeads (Miltenyi) and labeled with 1 μM CFSE (Invitrogen) in PBS containing 0.1% FCS at 37° C. for 7 minutes. After washing, T cells were resuspended to $5\times10^5$ cells/ml in RF-10 and mixed with stimulator beads (T cell activation/expansion kit; Miltenyi) at $2.5\times10^5$ beads/ml. For microwell cultures, 100 μl of T cell/bead mixture were plated into the wells of a round-bottom 96-well culture plate and graduated numbers of tumour cells (irradiated 80Gy) or Treg (purified from PBMC using Miltenyi Treg isolation kit according to the manufacturer's instructions) added in a 100 μl volume. Alternatively, to assess the requirement for direct cell contact, $3\times10^5$ tumor cells were plated into duplicate wells of a 24-well culture plate and 100 μl of the T cell/bead mixture added either directly to the well ('co-culture') or to the upper chamber of a 0.4 μm Transwell® insert (Corning; Lowell, Mass.) ('separated'). Cells were cultured for 4 days and then analysed by flow cytometry, using the 'proliferation' algorithm in FlowJo to model the percent divided. This value was then used to calculate percent suppression according to the following formula: 100×(1−[test/control]), where 'control' was the result of T cells cultured in the absence of any suppressor cells. Tumor cells and Treg were all allogeneic to the responding T cells.

RNA Isolation and cDNA Synthesis

Total RNA was extracted using the RNeasy® Mini Kit (Qiagen, Hilden, Germany) according to the manufacturer's instructions and immediately stored at −80° C. Complimentary DNA (cDNA) was synthesized from 1 μg total RNA in a 20 μL reaction for 60 min at 42° C. The reaction consisted of 1 μg random hexamer primers (Promega, Madison, Wis.), 4 mM $MgCl_2$, 1 mM deoxynucleoside triphosphates (Applied Biosystems, Foster City, Calif.), 40 units of RNase inhibitor (Promega) and 10 units of Moloney murine leukemia virus reverse transcriptase (Invitrogen).

PCR, Gel Electrophoresis and DNA Sequencing

In each 25 μl reaction, 1 μl of cDNA was used together with final concentrations of 2 mM $MgCl_2$, 0.2 mM deoxynucleoside triphosphates (Applied Biosystems), 0.625 units of Amplitaq Gold DNA polymerase (Applied Biosystems) and 2 ng of primers (Sigma-Genosys, Castle Hill, NSW, Australia). Primer sequences were as follows:

```
FOXP3 (forward primer)
5'-GCCCTTGGACAAGGACCCGATG-3';      (SEQ ID NO: 2)

FOXP3 (reverse primer)
5'-CATTTGCCAGCAGTGGGTAGGA-3';      (SEQ ID NO: 3)

CYCLOPHILIN-A (forward primer)
5'-GTCAGCAATGGTGATCTTCTT-3';       (SEQ ID NO: 9)

CYCLOPHILIN-A (reverse primer)
5'-GCAGAAAATTTTCGTGCTCTG-3'.       (SEQ ID NO: 10)
```

PCR involved 35 cycles (or 40 cycles, where stated) at 94° C. for 1 minute, 66° C. for 1 minute, 72° C. for 1 minute and a final primer extension at 72° C. for 10 minutes. PCR products were resolved using 1% agarose gel electrophoresis. Where required for sequencing, PCR products were cut from agarose gels and purified with Qiaquick gel extraction kits (Qiagen) according to the manufacturer's instructions. Purified DNA was sequenced at the Micromon DNA Sequencing Facility (Monash University, VIC, Australia).

Quantitative PCR

Quantitative PCR was performed using an ABI 7700 Prism Sequence Detector (Applied Biosystems). Thermal cycle conditions were set at 50° C. for 2 minutes, 95° C. for 10 minutes followed by 40 cycles of 94° C. for 20 seconds and 60° C. for 45 seconds. Samples were run in duplicate, and relative expression of FOXP3 was determined by normalizing to 18S expression in order to calculate a fold change in value. FOXP3 primer sequences were as follows:

(left primer) 5'-ACCTACGCCACGCTCATC-3' (SEQ ID NO:7);

(right primer) 5'-TCATTGAGTGTCCGCTGCT-3' (SEQ ID NO:8) with FOXP3 probe number 51 from the Roche Universal Probe Library. We calculated the relative mRNA expression using the target threshold ($C_T$) value for reference as a calibrator.

Western Blot

Whole cell lysates from $2\times10^6$ cells were prepared by sonication in 100 μL lysis buffer containing 0.05% SDS, 50 mM Tris pH 7.5, 5 mM EDTA, 0.5% Sodium Deoxycholate, 150 mM NaCl, 10 mM NaF and protease inhibitors. Samples were heated and approximately 204 per sample ($4\times10^5$ cell equivalents) were dissolved in 4× NuPAGE LDS Sample Buffer supplemented with NuPAGE Sample Reducing Buffer (both from Invitrogen) and heated at 70° C. for 10 minutes. Equal volumes of lysates were subjected to LDS-PAGE using NuPAGE 4-12% Bis-Tris gels under reducing conditions in MES-SDS running buffer supplemented with NuPAGE Antioxidant (all materials from Invitrogen) at 150V. SeeBlue® Plus2 Pre-Stained Standard (10 μl) was loaded into one lane.

Resolved proteins were transferred onto 8×7.5 cm membrane (, Billerica, Mass.) in Trans-Blot® Semi-Dry buffer (Bio-Rad Laboratories, Hercules, Calif.) for 15 minutes at 15V constant using NuPAGE transfer buffer (Invitrogen). The membranes were blocked with 5% nonfat dry milk in 1×TBS for 1 hour at room temperature, then probed with 2 μg/ml anti-FoxP3 (clone PCH101; eBioscience) overnight at 4° C. After several washes with 1×TBS/0.01% Tween 20 (TBS-T), the membranes were incubated with a 1:10,000 dilution of HRP-conjugated goat anti-rat-IgG secondary (Chemicon) for 1 hour at room temperature, followed by extensive washes with TBS-T.

The membranes were treated with a working solution of ECL Plus Western Blotting Detection kit (Amersham Biosciences, Buckinghamshire, UK) for 5 minutes at room temperature. We then used STORM 840 v2005 (Amersham Biosciences) to detect the immunoreactive bands at 100 microns pixel size with normal sensitivity, followed by analysis via ImageQuant TL Software v2003 (Amersham Biosciences). Subsequently, membranes were washed in TBS-T for 1 hour at room temperature, and re-probed with rabbit antibody to β-actin (Cell Signalling, Danvers, Mass.) diluted 1:1,000 overnight at 4° C. After several washes with TBS-T, the membranes were incubated with a 1:20,000 dilution of HRP-conjugated sheep anti-rabbit-IgG secondary (Chemicon) for 1 hour at room temperature, followed by extensive washes with TBS-T. The membranes were then developed as described above.

Introduction

FoxP3 is a transcription factor that regulates the development and function of $CD4^+CD25^+$ T regulatory ($T_{reg}$) cells. Generally, $T_{reg}$ cells represent approximately 5% of the $CD4^+$ T cells in human blood and are essential in maintaining immune homeostasis via $T_{reg}$ cell-mediated immune suppression, and as such, may contribute to tumor immune escape. We recently observed for the first time that FoxP3 expression in melanoma tissue was not only restricted to the infiltrating $T_{reg}$, but was also expressed within the tumor cells. Therefore, we hypothesized that the expression of FoxP3 during tumorigenesis may result in tumor immunological tolerance. We verified FoxP3 expression in a large number of melanoma cell lines using flow cytometry, reverse-transcription PCR and Western blot. Furthermore, we extended the study with tumor cell lines from other types of malignancies and demonstrated that the majority expressed FoxP3. In contrast, we showed that normal primary cell lines did not express FoxP3, supporting the association of FoxP3 expression with tumorigenesis. Meanwhile, we discovered a novel third splice isoform of FoxP3, which was not only expressed in tumour cells but also in the brain and testis, suggesting that these tissues may establish an immune privilege-like site by expressing FoxP3. In conclusion, our data reveal that tumor cells express the transcription factor FoxP3, which may provide a survival advantage by setting in motion an immunosuppressive genetic program that inhibits the generation of an effective anti-tumor immune response.

Full Coding Sequence of FoxP3 from Database (Accession Number NM_014009):

SEQ ID NO:1 (shown without introns, but indicating the location and length of introns)

- non-quantitative PCR primer positions are indicated in bold
- real-time PCR primer positions are underlined
- start positions of siRNA sequences are indicated in italics and underlining FOXP3 > hg2B_knownGene_NM_014009
range = chrX:48994354-49008232

(UTR)

GCACACACTCATCGAAAAAAATTTGGATTATTAGAAGAGAGAGGTCTGCG

GCTTCCACACCGTACAGCGTGGTTTTTCTTCTCGGTATAAAAGCAAAGTT

GTTTTTGATACGTGACAGTTTCCCACAAGCCAGGCTGATCCTTTTCTGTC

AGTCCACTTCACCAAG

Intron 6238 bps (EXON 1)

CCTGCCCTTGGACAAGGACCCGATGCCCAACCCCAGGCCTGGCAAGCCCT

CGGCCCCTTCCTTGGCCCTTGGCCCATCCCCAGGAGCCTCGCCCAGCT<u>*G*</u>G

AGGGCTGCACCCAAAGCCTCAGACCTGCTGGGGGCCCGGGGCCCAGGGGG

AACCTTCCAGGGCCGAGATCTTCGAGGCGGGGCCCATGCCTCCTCTTCTT

CCTTGAACCCCATGCCACCATCGCAGCTGCAG

Intron 527 bps (EXON 2)

CTGCCCACACTGCCCCTAGTCATGGTGGCACCCTCCGGGGCACGGCTGGG

CCCCTTGCCCCACTTACAGGCACTCCTCCAGGACAGGCCACATTTCATGC

ACCAG

Intron 98 bps (EXON 3)

CTCTCAACGGTGGATGCCCACGCCCGGACCCCTGTGCTGCAGGTGCACCC

CCTGGAGAGCCCAGCCATGATCAGCCTCACACCACCCACCACCGCCACTG

GGGTCTTCTCCCTCAAGGCCCGGCCTGGCCTCCCACCTG

Intron 424 bps (EXON 4)

GGATCAACGTGGCCAGCCTGGAATGGGTGTCCAGGGAGCCGGCACTGCTC

TGCACCTTCCCAAATCCCAGTGCACCCAGGAAGGACAG

Intron 69 bps (EXON 5)

CACCCTTTCGGCTGTGCCCCAGAGCTCCTACCCACTGCTGGCAA<u>*A*</u>TGGTG

TCTGCAAGTGGCCCGGATGTGAGAAGGTCTTCGAAGAGCCAGAGGACTTC

CTCAA

Intron 944 bps (EXON 6)

GCACTGCCAGGCGGACCATCTTCTGGATGAGAAGGGCAGGGCACAATGTC

TCCTCCAGAGAGAGATGGTACAGTCTCTGGAGCAGCAG

Intron 205 bps (EXON 7)

CTGGTGCTGGAGAAGGAGAAGCTGAGTGCCATGCAGGCCCACCTGGCTGG

GAAAATGGCACTGACCAAGGCTTCATCTGTG

Intron 1361 bps (EXON 8)

GCATCATCCGACAAGGGCTCCTGCTGCATCGTAGCTGCTGGCAGCCAAGG

CCCTGTCGTCCCAGCCTGGTCTGGCCCCCGGGAGGCCCCTGACAGCCTGT

TTGCTGTCCGGAGGCACCTGTGGGGTAGCCATGGAAACAGCACATTCCCA

G

Intron 714 bps (EXON 9)

AGTTCCTCCACAACATGGACTACTTCAAGTTCCACAACATGCGACCCCCT

TTC<u>ACCTACGCCACGCTCATC</u>CGCTGG

-continued

```
Intron 1360 bps
                                                (EXON 10)
GCCATCCTGGAGGCTCCAGAGAAGCAGCGGACACTCAATGAGATCTACCA

CTGGTTCACACGCATGTTTGCCTTCTTCAGAAACCATCCTGCCACCTGGA

AG

Intron 180 bps
                                                (EXON 11)
AACGCCATCCGCCACAACCTGAGTCTGCACAAGTGCTTTGTGCGGGTGGA

GAGCGAGAAGGGGGCTGTGTGGACCGTGGATGAGCTGGAGTTCCGCAAGA

AACGGAGCCAGAGGCCCAGCAGGTGTTCCAACCCTACACCTGGCCCCTGA

CCTCAAGATCAAGGAAAGGAGGATGGACGAACAGGGGCCAAACTGGTGGG

AGGCAGAGGTGGTGGGGGCAGGGATGATAGGCCCTGGATGTGCCCACAGG

GACCAAGAAGTGAGGTTTCCACTGTCTTGCCTGCCAGGGCCCCTGTTCCC

CCGCTGGCAGCCACCCCCTCCCCCATCATATCCTTTGCCCCAAGGCTGCT

CAGAGGGGCCCCGGTCCTGGCCCCAGCCCCCACCTCCGCCCCAGACACAC

CCCCCAGTCGAGCCCTGCAGCCAAACAGAGCCTTCACAACCAGCCACACA

GAGCCTGCCTCAGCTGCTCGCACAGATTACTTCAGGGCTGGAAAAGTCAC

ACAGACACACAAAATGTCACAATCCTGTCCCTCAC
```

Example 1

FoxP3 is Expressed by Both Lymphocytes and Tumor Cells in Metastatic Melanoma Tissue With the aim of characterizing the frequency and localization of Treg in melanoma, we performed immunohistochemistry (IHC) on metastatic melanoma tissue sections using a polyclonal anti-FoxP3 antibody. Surprisingly, in addition to the expected staining of cells with lymphocyte morphology (small, round, dense nucleus and little cytoplasm), staining was also occasionally apparent in cells which had several morphological features of tumor cells, such as a large, irregular nucleus and abundant cytoplasm (FIG. 1*a*). Although unexpected, this staining appears to be specific, given the nuclear localization of the signal and the lack of staining with control rabbit IgG (not shown). Furthermore, this is not an isolated phenomenon, as $FoxP3^+$ tumor cells were detectable in four additional biopsy specimens from different patients and various sites of metastasis.

This preliminary analysis therefore suggested that a proportion of $FoxP3^+$ cells in melanoma tissue represent the tumor cells themselves, not Treg. To definitively identify these $FoxP3^+$ cells as melanoma cells, two-color IHC was performed using antibodies to both FoxP3 and Melan-A, a specific marker of melanocytic differentiation (21). As shown in FIG. 1*b*, $FoxP3^+$ cells were readily identified within $Melan\text{-}A^+$ tumor cell islands, whereas infiltrating Treg were located outside of these islands and lacked staining for Melan-A. These results therefore provide further evidence that, in addition to Treg, melanoma cells can also express FoxP3.

To our knowledge, the expression of FoxP3 by cells outside of the T cell lineage has not been previously reported, except in pancreatic carcinoma cells (Hinz et al., Cancer Res. 2007; 67(17):8344-50; Hinz, S; Pagerols-Raluy, L; Ammerpohl, O; Oberg, H H; Wesch, D; Kabelitz, D; Gruetzman, R; Faendrich, F; Kalthoff, H., Significance of the expression of the Treg marker FoxP3 in pancreatic carcinoma cells with regard to an immunomodulatory action on nave T cells. 123rd Congress of the German Society for Surgery, Berlin; 2-5 May, 2006).

Figure 2:
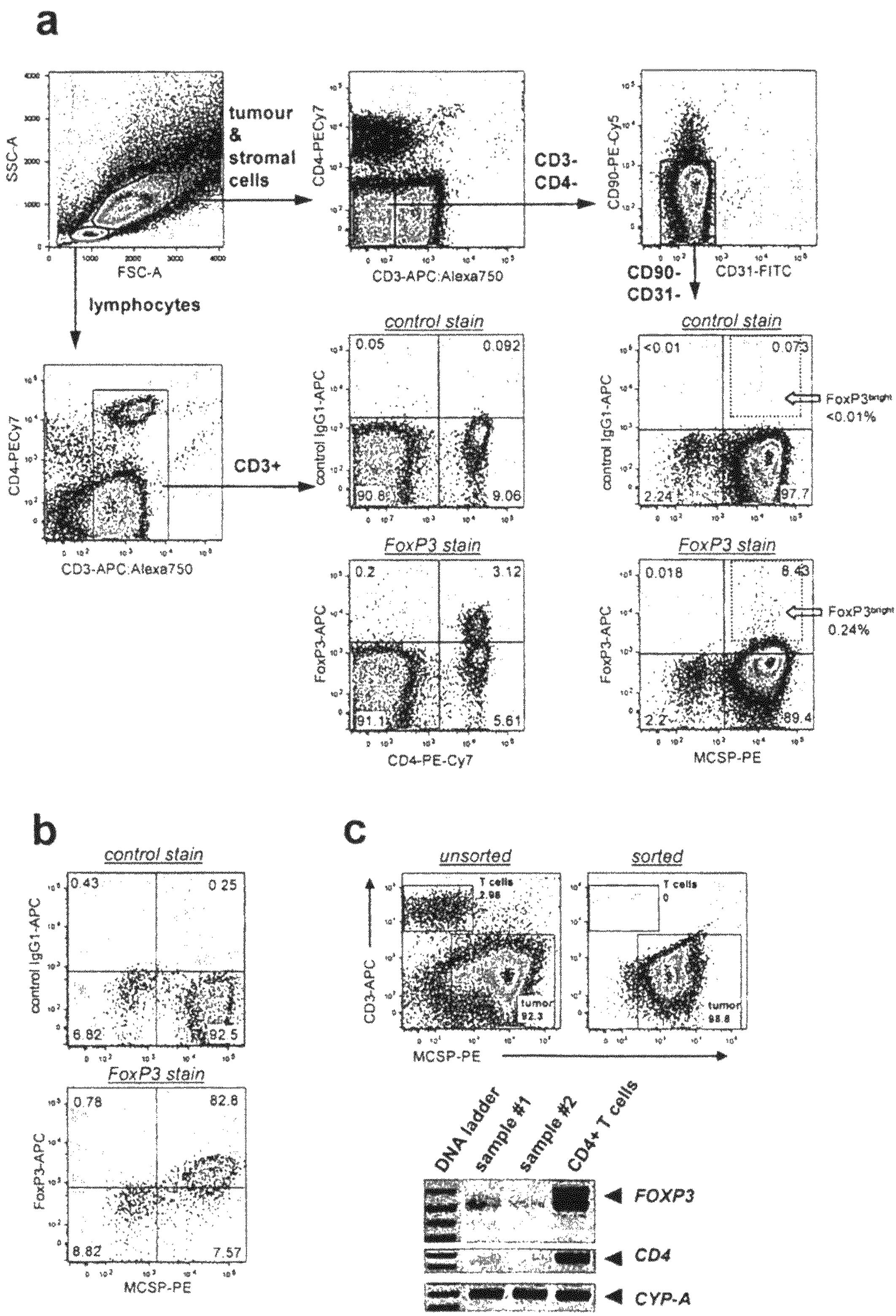
FIG. 2: Detection of FoxP3 in metastatic melanoma tissue using flow cytometry. Cell suspensions were generated from metastatic melanoma tumor tissue and stained for flow cytometric analysis. (a): representative analysis, showing hierarchical gating strategy for identification of tumor cells and T cells. For each gated population, staining with anti-FoxP3 mAb or an isotype matched negative control is shown. Quadrant markers were set on the basis of isotype control staining, while the region indicated by the dotted line was set to identify FoxP3$^{bright}$ tumor cells. (b): A second sample (gated on CD3−CD4−CD31−CD90−), illustrating FoxP3 staining of the entire melanoma cell population. (c): tumor cells were sorted from disagregated tumor tissue and expression of mRNA for FOXP3, CD4 and the housekeeping gene CYP-A was assessed by RT-PCR. Peripheral blood CD4+ T cells are shown for comparision. Expression of CD3 and MCSP was determined by flow cytometry after sorting to confirm that the FOXP3 transcripts did not originate from Treg (sample #1 is shown).

To confirm the immunohistochemical results of our IHC studies, we generated cell suspensions from disaggregated melanoma tissue and analyzed them using 6-color flow cytometry, using a hierarchical gating strategy to unambiguously identify both melanoma cells and $CD4^+$ T cells within the mixed cell population (FIG. 2). To identify melanoma cells, T cells were first excluded on the basis of forward and side scatter and then by gating out $CD3^+$ and $CD4^+$ events. Endothelial cells and tissue fibroblasts were excluded by gating out $CD31^+$ and $CD90^+$ events, respectively, and melanoma cells within the remaining population were identified by staining for MCSP (melanoma chondroitin sulfate proteoglycan), a marker widely expressed in melanoma (22). Fluorescence minus one (FMO) isotype-matched negative controls were used to assess the level of background staining within this population, and this pattern compared to staining with anti-FoxP3. Generally, the addition of anti-FoxP3 produced a shift of the entire $MCSP^+$ population compared to the control; the magnitude of this shift varied greatly, ranging from barely detectable to >1 log shift. In addition, many samples had a small sub-population of $FoxP3^{bright}$ cells that clearly expressed much higher levels of FoxP3 than the bulk population. The examples shown in FIG. 2*a-b* illustrate these different patterns; the sample in part (a) demonstrates only a slight shift of the entire population but a distinct population of $FoxP3^{bright}$ cells, while the sample in part (b) was characterized by a prominent shift of the entire population but no distinct subset of $FoxP3^{bright}$ cells. For the 7 samples analyzed, the mean proportion of $FoxP3^{bright}$ cells was 0.1±0.09% (SD, range 0-0.24%). This population likely corresponds to the scattered $FoxP3^+$ melanoma cells identified in IHC analysis of tissue sections.

The proportion of Treg was also determined for each sample by gating on $CD3^+$ $CD4^+$ cells within the lymphocyte gate (FIG. 2*a*). Similar to previous studies (9, 10), the proportion of $CD4^+$ T cells staining positive for FoxP3 in melanoma tissue was remarkably high, with a mean value of 21.1±14.3% (range 5.8-41.1%). These $FoxP3^+$ T cells were also $CD25^+$ and $CD127^{neg/lo}$, thereby confirming their identity as Treg (not shown). No obvious correlation was observed between the proportion of Treg and the proportion of $FoxP3^{bright}$ melanoma cells.

In order to confirm that melanoma cells expressed FOXP3 transcripts, the disrupted tumor tissue was subject to high-stringency cell sorting to purify the melanoma cells (identified as $MCSP^+$ $CD3^-$ $CD4^-$ $CD31^-$ $CD90^-$) and these cells were subject to RT-PCR analysis (FIG. 2*c*). PCR using primers specific for the housekeeping gene CYCLOPHILIN-A (CYPA) produced a band of the expected size for both specimens, confirming the integrity of the cDNA. PCR using FOXP3 primers produced a pattern of bands similar—but not identical—to that observed for CD4+Treg (see later), thus confirming the presence of FOXP3 transcripts in sorted melanoma cells. Importantly, analysis of the sorted populations confirmed that they were >98% $MCSP^+$ and that the level of T cell contamination was <0.005%. PCR amplification using primers for CD4 revealed no product for sample #2 and, while a faint band was detectable for sample #1, no T cells were detected by flow cytometry, suggesting that these CD4 transcripts likely originate from contaminating DCs or monocyte/macrophages, not Treg. Thus, FOXP3 transcripts can be amplified from pure, freshly isolated melanoma cells, providing further evidence that these cells can express FoxP3.

Example 2

FoxP3 is Widely Expressed by Melanoma Cell Lines

Figure 3:
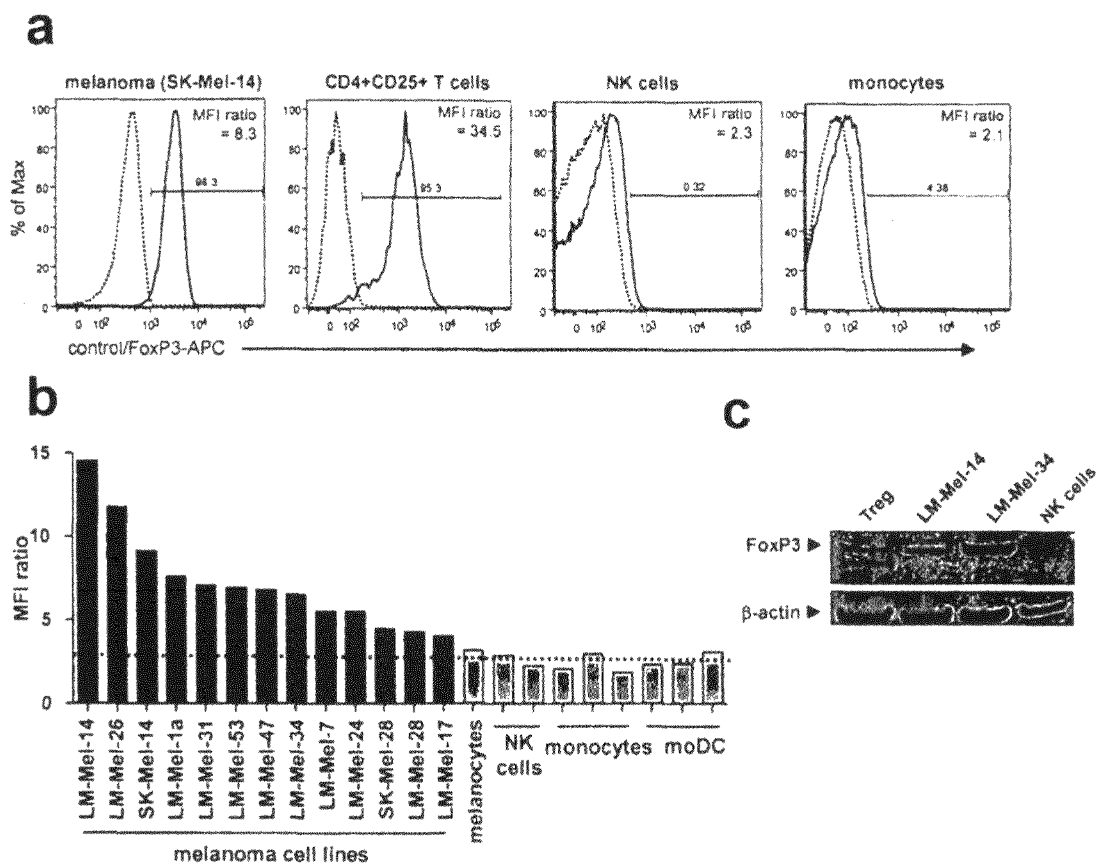
FIG. 3: FoxP3 is widely expressed in melanoma cell lines. (a-b): Cells were stained using anti-FoxP3 mAb (solid line) or isotype-matched negative control (broken line) and analysed by flow cytometry. In (a), one representative melanoma cell line (SK-Mel-14) is shown, together with peripheral blood CD4+CD25+ T cells, NK cells and monocytes for comparison. In (b), results for a panel of melanoma cell lines are shown (black bars), together with a range of negative controls (peripheral blood NK cells/monocytes, and 7-day cultured monocyte-derived DCs; grey bars). For each sample, the MFI was determined following staining with anti-FoxP3 and isotype control and the ratio calculated. (c): Western blot analysis of lysates prepared from a short-term expanded Treg cell line, two melanoma cell lines and peripheral blood NK cells.

The results presented thus far demonstrate, using a variety of methods, that cells with the morphology and surface marker phenotype of melanoma can express FoxP3. However, the identification of melanoma cells within a mixed population using these criteria is not unequivocal. Further confirmation of FoxP3 expression in melanoma cells was obtained by analyzing a panel of established melanoma cell lines by flow cytometry (FIG. 3) after staining with anti-FoxP3 mAb. The melanoma cell line shown in FIG. 3*a* (SK-Mel-14) was uniformly positive for FoxP3, although the intensity of staining was not quite as high as for $CD4^+$ $CD25^+$ T cells. Staining of freshly isolated blood NK cells and monocytes was negative, as expected.

Staining for FoxP3 on additional melanoma cell lines is summarized in FIG. 3*b*. For all cell lines analyzed, staining with anti-FoxP3 resulted in a shift in the fluorescence of the entire population compared to the isotype control, but the magnitude of this shift varied substantially. In order to quantify the intensity of staining, the mean fluorescence intensity (MFI) was determined following staining with anti-FoxP3 or isotype control and a ratio of the two values calculated. This calculation was necessary to normalize the different levels of background fluorescence amongst the various cell lines. The same calculation was also performed for a range of negative control cells (freshly isolated blood NK cells and monocytes, and 7-day cultured monocyte-derived dendritic cells) in order to establish the background MFI ratio (indicated by a dotted line). The majority of melanoma cell lines had MFI ratios well above this background level, although the intensity of FoxP3 expression varied considerably and a small proportion of cell lines had ratios only slightly above background. In contrast, cultured normal epidermal melanocytes did not express detectable levels of FoxP3. Expression of FoxP3 protein was further confirmed in melanoma cell lines using Western blotting (FIG. 3*c*). As previously described, lysates from Treg cells ran as a closely spaced doublet, corresponding to full-length FoxP3 and a splice variant lacking exon 2, respectively (14, 15). In melanoma cells, a band corresponding to full-length FoxP3 (but not the Δ2 variant) was also readily detectable. Thus, FoxP3 is widely expressed in melanoma cell lines (but not normal melanocytes); however, the intensity of expression is variable and a small number of melanoma cell lines express only borderline levels of FoxP3.

Example 3

The FOXP3 Gene is Expressed in Melanoma Cells as Three Distinct mRNA Variants, One of which is Predicted to Encode a Novel Protein To confirm FOXP3 gene expression in melanoma cells, RNA was extracted from a panel of melanoma cell lines and used to generate cDNA by reverse transcription, which was then subject to PCR using primers specific for FOXP3 or the housekeeping gene CYP-A (cyclophilin-A). PCR products could be readily detected following amplification using FOXP3-specific primers (35 cycles), confirming that melanoma cell lines express FOXP3 mRNA (FIG. 4*a*).

Previous reports have demonstrated that, in Treg, FOXP3 mRNA is expressed as two variants: full-length and an alternatively spliced version lacking exon 2 (Δ2) (11, 15, 23). Using our primers, these two products would be expected to result in band sizes of 608 and 503 bp, respectively, and for $CD4^+$ T cells these two bands were observed as expected (FIG. 4*a*). For melanoma cells, however, an additional band (~100 bp smaller than the Δ2 product) was frequently detected which was not apparent in Treg. To better visualize this band, the PCR was repeated for selected cell lines at 40 cycles instead of 35 cycles (FIG. 4*b*). This analysis confirmed the presence of a third PCR product in melanoma cells which was absent from both freshly purified $CD4^+$ T cells and a Treg cell line expanded in culture for several weeks. Sequencing of this third band from one melanoma cell line (LM-Mel-34) revealed that this product was lacking both exons 2 and 3, and therefore corresponds to a novel FOXP3 mRNA variant (Δ2, 3; FIG. 4*c*). As expected, sequencing of the upper (608 bp) band confirmed that it was identical to the published sequence for fill-length FOXP3.

The previously described A2 splice variant contains an in-frame excision of exon 2 (105 bp), which is predicted to result in removal of part of the repressor domain of the normal FoxP3 protein without affecting sequences downstream of the second exon (11, 15). In contrast, the novel Δ2,3 isoform contains a 244 bp excision which is expected to result in a translation frame-shift.

The three isoforms of FoxP3 mRNA amplified and sequenced are as follows:

```
Full-length (608 bps) (SEQ ID NO: 4)
                                        EXON 1 (229bps)
GCCCTTGGACAAGGACCCGATGCCCAACCCCAGGCCTGGCAAGCCCTCGG

CCCCTTCCTTGGCCCTTGGCCCATCCCCAGGAGCCTCGCCCAGCTGGAGG

GCTGCACCCAAAGCCTCAGACCTGCTGGGGGCCCGGGGCCCAGGGGGAAC

CTTCCAGGGCCGAGATCTTCGAGGCGGGGCCCATGCCTCCTCTTCTTCCT

TGAACCCCATGCCACCATCGCAGCTGCAG

                                       EXON 2 (105 bps)
CTGCCCACACTGCCCCTAGTCATGGTGGCACCCTCCGGGGCACGGCTGGG

CCCCTTGCCCCACTTACAGGCACTCCTCCAGGACAGGCCACATTTCATGC

ACCAG

                                       EXON 3 (139 bps)
CTCTCAACGGTGGATGCCCACGCCCGGACCCCTGTGCTGCAGGTGCACCC

CCTGGAGAGCCCAGCCATGATCAGCCTCACACCACCCACCACCGCCACTG

GGGTCTTCTCCCTCAAGGCCCGGCCTGGCCTCCCACCTG

                                        EXON 4 (88 bps)
GGATCAACGTGGCCAGCCTGGAATGGGTGTCCAGGGAGCCGGCACTGCTC

TGCACCTTCCCAAATCCCAGTGCACCCAGGAAGGACAG

                                        EXON 5 (47 bps)
CACCCTTTTCGGCTGTGCCCCAGAGCTCCTACCCACTGCTGGCAAATG

Δ2 splice variant (503 bps) (SEQ ID NO: 5)
                                       EXON 1 (229 bps)
GCCCTTGGACAAGGACCCGATGCCCAACCCCAGGCCTGGCAAGCCCTCGG

CCCCTTCCTTGGCCCTTGGCCCATCCCCAGGAGCCTCGCCCAGCTGGAGG

GCTGCACCCAAAGCCTCAGACCTGCTGGGGGCCCGGGGCCCAGGGGGAAC

CTTCCAGGGCCGAGATCTTCGAGGCGGGGCCCATGCCTCCTCTTCTTCCT

TGAACCCCATGCCACCATCGCAGCTGCAG
```

-continued

EXON 3 (139 bps)
CTCTCAACGGTGGATGCCCACGCCCGGACCCCTGTGCTGCAGGTGCACCC

CCTGGAGAGCCCAGCCATGATCAGCCTCACACCACCCACCACCGCCACTG

GGGTCTTCTCCCTCAAGGCCCGGCCTGGCCTCCCACCTG

EXON 4 (88 bps)
GGATCAACGTGGCCAGCCTGGAATGGGTGTCCAGGGAGCCGGCACTGCTC

TGCACCTTCCCAAATCCCAGTGCACCCAGGAAGGACAG

EXON 5 (47 bps)
CACCCTTTCGGCTGTGCCCCAGAGCTCCTACCCACTGCTGGCAAATG

Δ2, 3 splice variant (364 bps) (SEQ ID NO: 6)

EXON 1 (229 bps)
GCCCTTGGACAAGGACCCGATGCCCAACCCCAGGCCTGGCAAGCCCTCGG

CCCCTTCCTTGGCCCTTGGCCCATCCCCAGGAGCCTCGCCCAGCTGGAGG

GCTGCACCCAAAGCCTCAGACCTGCTGGGGGCCCGGGGCCCAGGGGGAAC

CTTCCAGGGCCGAGATCTTCGAGGCGGGCCCATGCCTCCTCTTCTTCCT

TGAACCCCATGCCACCATCGCAGCTGCAG

EXON 4 (88 bps)
GGATCAACGTGGCCAGCCTGGAATGGGTGTCCAGGGAGCCGGCACTGCTC

TGCACCTTCCCAAATCCCAGTGCACCCAGGAAGGACAG

EXON 5 (47 bps)
CACCCTTTCGGCTGTGCCCCAGAGCTCCTACCCACTGCTGGCAAATG

The predicted amino acid sequence is shown in FIG. **4*d***; this sequence is identical to FoxP3 in the N-terminal portion encoded by exon 1, but this region is followed by a 103aa sequence with no significant homology to FoxP3 (or any other sequence in the public databases) and a premature stop codon, resulting in a protein that is approximately half the size of FoxP3.

Example 4

FoxP3 is Also Expressed in Cell Lines Derived from Other Types of Solid Tumor Given that FoxP3 was widely expressed in melanoma cell lines, we were interested to determine if cell lines derived from other types of solid tumor also expressed FoxP3. Accordingly, an extensive panel of tumor cell lines was examined for FoxP3 expression by flow cytometry; this panel comprised 3-4 cell lines each from colon cancer, lung cancer, breast cancer, prostate cancer, glioblastoma, renal cell carcinoma and bladder cancer (FIG. **5*a*). As per the melanoma cell lines, the intensity of FoxP3 expression was determined relative to isotype control staining and calculated as an MFI ratio. The grey region indicates the mean background MFI ratio as determined in FIG. 3*b***; any measurement falling within, or very close to, this region cannot be considered positive for FoxP3.

This analysis revealed that at least one cell line from each type of tumor expressed readily detectable levels of FoxP3. Some, such as prostate cancer and colon cancer, were uniformly positive, whereas others, such as breast cancer, appeared to express FoxP3 less frequently. However, given the small sample size for each type of cancer, these differences cannot be considered conclusive. Early passage cultures of normal fibroblasts (derived from dermis or foreskin) lacked convincing staining for FoxP3, suggesting that the expression of FoxP3 is restricted to malignant cell lines. Interestingly, however, extended culture of fibroblasts did eventually result in induction of FoxP3 expression (FIG. **5*a***). The mechanism responsible for this observation is unclear at present, although it is possible that FoxP3 is induced in normal tissue cells as they approach replicative senescence, or in response to extended culture under non-physiological conditions. Support for the latter possibility comes from a comparison of FoxP3 expression in matched melanoma biopsies and cell lines derived from them, which revealed a much higher frequency of FoxP3$^+$ cells in the cell line than the original tissue (data not shown). However, it is unclear at present whether this reflects genuine modulation of FoxP3 expression in culture or selective expansion of rare FoxP3$^+$ melanoma cells.

To confirm expression of FOXP3 transcripts, one cell line from each type of cancer was selected on the basis of unequivocal expression of FoxP3 protein by flow cytometry and analyzed by RT-PCR. As shown in FIG. **5*b*, each cell line tested positive for FOXP3, and several cell lines also expressed the Δ2,3 isoform described in FIG. 4**. Thus, the expression of FoxP3 in tumor cell lines is not restricted to melanoma cells.

Example 5

Figure 4:
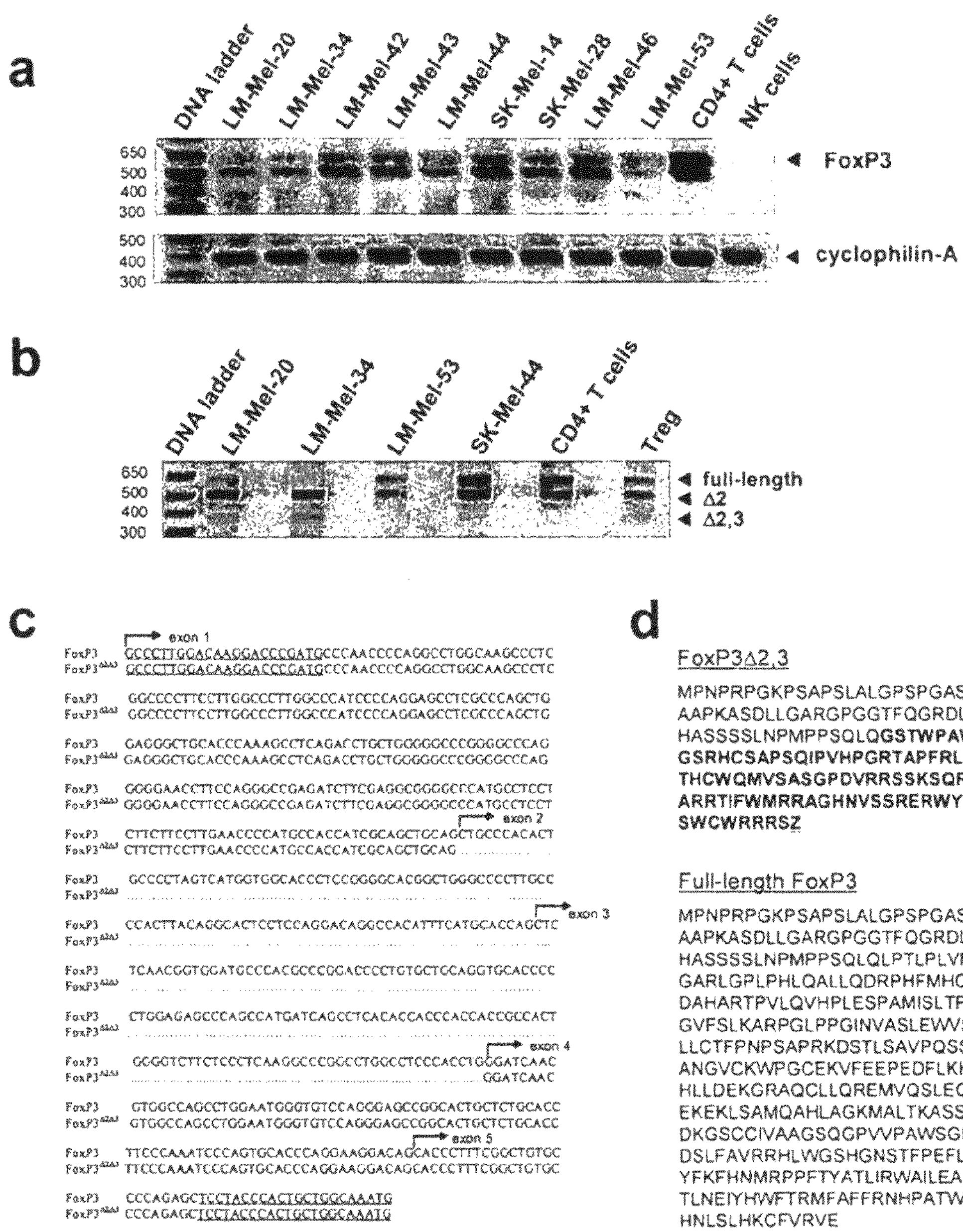
FIG. 4: FoxP3 mRNA is expressed as 3 distinct isoforms in melanoma cells. (a): RNA extracted from $1\times10^6$ cells was reverse transcribed and the cDNA amplified by PCR (35 cycles) using primers specific for FOXP3 and CYP-A. Shown are representative melanoma cell lines and MACS-purified peripheral blood CD4+ T cells and NK cells. (b): FOXP3 PCR was repeated at 40 cycles, to better visualize the third PCR product. Shown are 4 melanoma cell lines, MACS-purified peripheral blood $CD4^+$ T cells and a short-term expanded Treg cell line. (c): Sequence of the upper (608 bp; SEQ ID NO:4) and lower (364 bp; Δ2,3; SEQ ID NO:6) FOXP3 PCR products. Primer sites are underlined. (d): Predicted amino acid sequence of the Δ⅔ isoform (SEQ ID NO:11), compared to the published protein sequence for full-length FoxP3 (SEQ ID NO:12). For the Δ⅔ isoform, the sequence in bold type differs from the wild type protein, and the premature stop codon is underlined.
Figure 6:
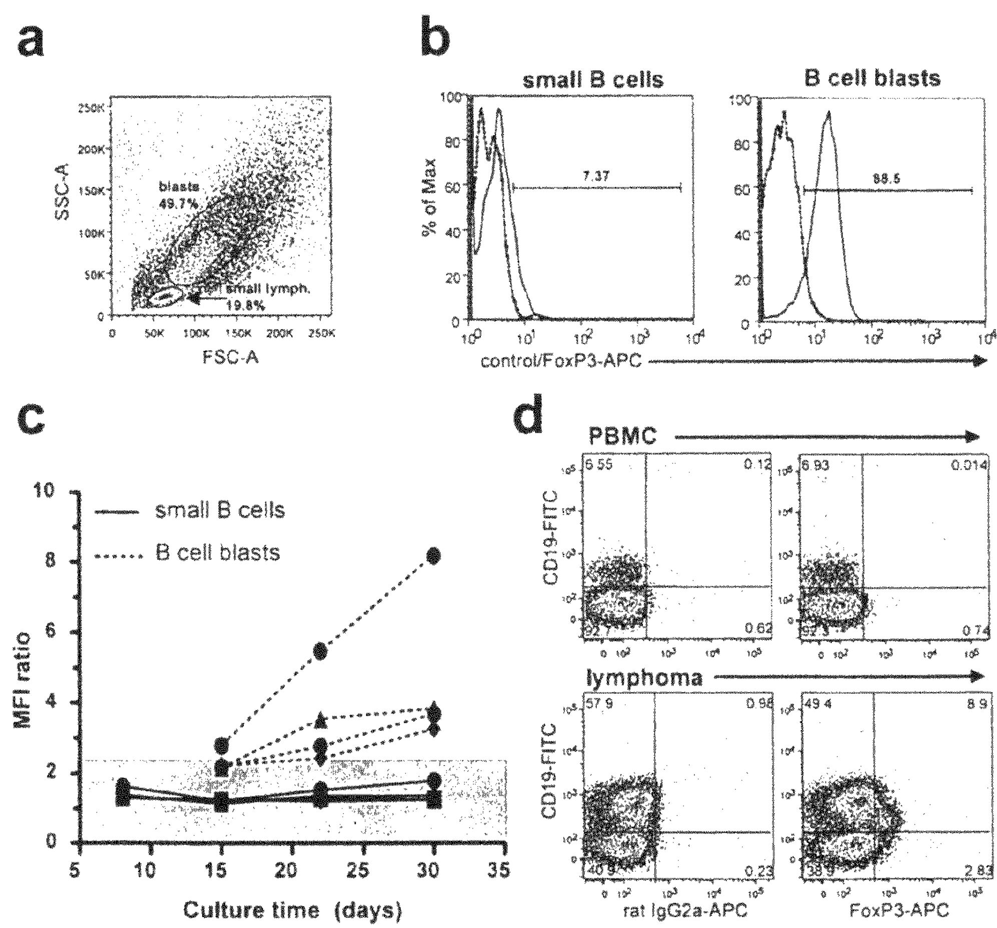
FIG. 6: De novo induction of FoxP3 expression during EBV transformation of B cells in vitro and in vivo. (a-c): PBMC from 4 healthy donors were infected with EBV in vitro and monitored for expression of FoxP3 by flow cytometry. After 30 days' culture, cells were gated into 'small lymphocyte' and 'blast' populations on the basis of forward and side scatter parameters (a), and the CD19+ B cells within each gate were assessed for FoxP3 expression (solid line) compared to staining with isotype matched control mAb (broken line)(b). In (c), a full time-course analysis of all 4 donors is shown. The B cell blast population is displayed from the first time point at which it was clearly detectable (day 15) (d): Analysis of PBMC and tumor cells from a patient with PTLD. Cells were stained for CD19 and either isotype control or anti-FoxP3 as indicated. Analysis is gated on CD4-negative lymphocytes.
Figure 8:
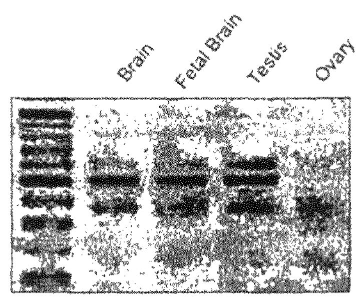
FIG. 8 shows that PCR amplification of cDNA from brain and testis tissue reveals three distinct foxp3 isoforms.

A Novel Isoform of FoxP3 can be Identified in Some Tumor Cell Lines as Well as Normal Testis and Brain Tissue As mentioned above, it was observed that some tumor cell lines expressed three distinct foxp3-derived transcripts, instead of the usual two as detected in $T_{reg}$ (see FIGS. 4 and 6). Further analysis of a panel of RNAs derived from normal tissues (Clontech) revealed that this third was also clearly detectable in adult testis and brain (but not ovary), as well as fetal brain tissue (FIG. 8). All other healthy tissue examined lacked this third band, although the two upper bands were often observed, presumably due to the presence of $T_{reg}$ in the vasculature. Sequencing of this band revealed that it lacked both exons 2 and 3 of the full-length transcript. To our knowledge, this isoform of foxp3 has not been previously described.

Figure 9:
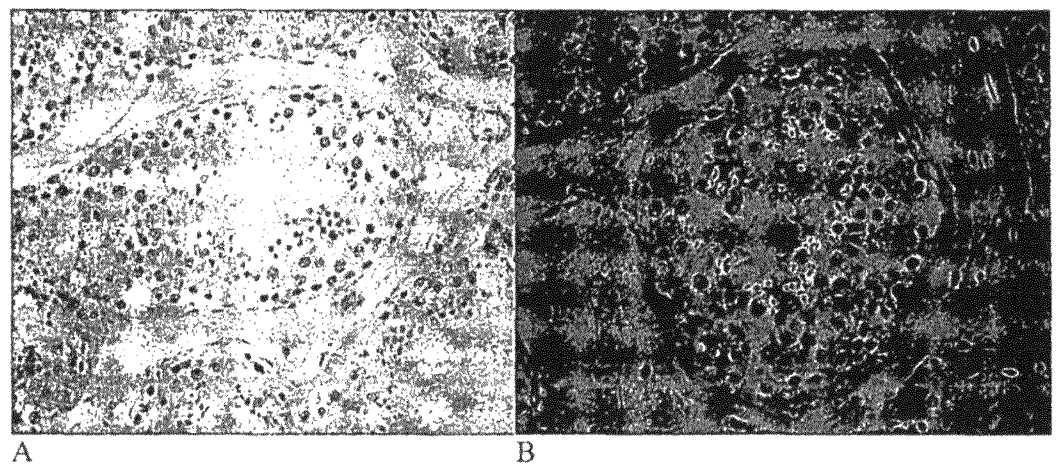
FIG. 9 depicts immunohistochemical staining of normal adult testis tissue for FoxP3 (FIG. 9A) and NY-ESO-1 (FIG. 9B).

In order to confirm the unexpected expression of foxp3 in testis, tissue sections were stained by immunohistochemistry (using the polyclonal anti-FoxP3 antiserum as used in FIG. 1). This analysis revealed strong FoxP3 expression in the germ cells near the basement membrane, while more differentiated cells lacked detectable FoxP3 expression (FIG. 9A). Interestingly, this expression pattern is virtually identical to that observed for cancer-testis (CT) antigens such as NY-ESO-1 (FIG. 9B). Thus, FoxP3 has a very similar distribution pattern to that of a CT antigen (being expressed in cancer and testis), raising the intriguing possibility of hierarchical or linked gene expression patterns.

Example 6

Expression of Foxp3 by Melanoma Cell Lines can be Modulated by siRNA-Mediated Gene Knockdown A small interfering RNA (siRNA) approach was used to knock-down foxp3 gene expression in melanoma cell lines. Knock-down of foxp3 gene expression was achieved using a commercially available siRNA reagent (FoxP30N-TARGET-plus SMARTpool®, from Dharmacon, cat#L-009307-00). This reagent consists of a pool of four siRNAs that have been modified to reduce off-target effects.

The approximate 5' start positions for the four siRNAs were provided by Dharmacon (which are indicated in underlined italics in the full-length sequence). The FoxP3 exons that are targeted are as follows:

| siRNA | start position | exon |
|---|---|---|
| Duplex 6: | 775 | 5 |
| Duplex 7: | 265 | 1 |
| Duplex 8: | 1270 | 10 |
| Duplex 9: | 1315 | 10 |

Real-time (quantitative) PCR was performed using the following FoxP3 primers:

```
Sense:
5'-ACCTACGCCACGCTCATC-3'       (SEQ ID NO: 7)

Antisense:
5'-TCATTGAGTGTCCGCTGCT-3'      (SEQ ID NO: 8)
```

Figure 10:
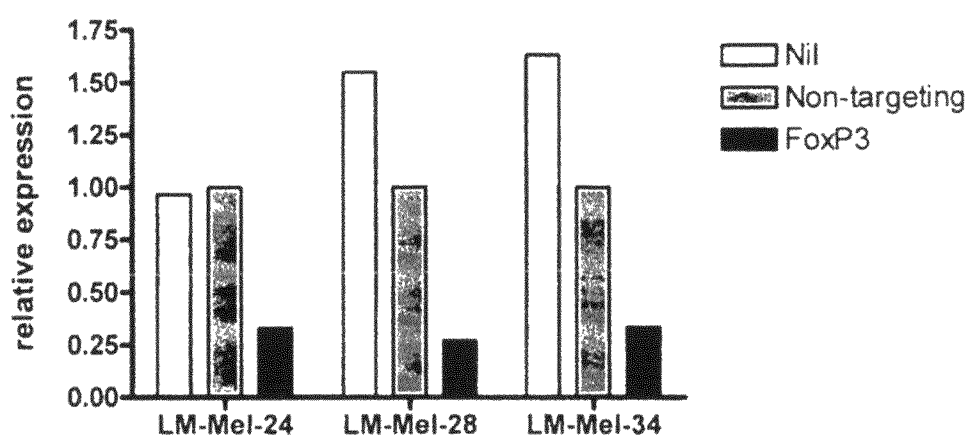
FIG. 10 shows real-time PCR measurement of foxp3 gene expression following transfection with control (non-targeting) or foxp3-specific siRNA constructs.

Preliminary results using real-time (quantitative) PCR revealed an approximately 75% reduction in gene expression following transfection with an siRNA targeted to foxp3, compared to that observed following transfection with a non-targeting control (FIG. 10). This therefore appears to be a valid approach by which to address the function of FoxP3 in tumor cells, which is a focus of additional experiments.

Example 7

Comparison of FoxP3 and NY-ESO-1 Expression in Tumour Cell Lines

The expression of FoxP3 and NY-ESO-1 was compared in tumour cell lines. A summary of the PCR results for the LM-MeI cell line series is presented in Table 1 below. There are only 2 melanoma cell lines that lacked FoxP3 expression (LM-Mel-7 and LM-Mel-47), as tested by RT-PCR. Both of these cell lines are negative for NY-ESO-1 expression by RT-PCR. However, we have had some recent data that may contradict the apparent lack of FoxP3 expression in LM-Mel-47, and are resolving this discrepancy.

TABLE 1

FoxP3 and NY-ESO-1 expression in melanoma cell lines

| Cell line (LM-Mel #) | ESO | FoxP3 |
|---|---|---|
| 1a | yes | yes |
| 5 | no | yes |
| 6 | no | yes |
| 7 | no | no |
| 8 | no | yes |
| 9 | no | yes |
| 10 | no | yes |
| 13 | no | yes |
| 14 | yes | yes |
| 17 | yes | yes |
| 19 | no | yes |
| 20 | no | yes |
| 22 | no | yes |
| 24 | no | yes |
| 25 | no | yes |
| 26 | no | yes |
| 27 | no | yes |
| 28 | yes | yes |
| 33 | no | yes |
| 34 | yes | yes |
| 36 | yes | yes |
| 37 | no | yes |
| 38 | no | yes |
| 39 | no | yes |
| 40 | yes | yes |
| 41 | yes | yes |
| 42 | yes | yes |
| 43 | no | yes |
| 44 | yes | yes |
| 45 | no | yes |
| 46 | no | yes |
| 47 | no | no |

The only other tumour cell lines to show low/absent FoxP3 expression so far are two bladder cancer lines. HT1197 is negative for ESO by RT-PCR, and negative for FoxP3 by both PCR and flow cytometry. The story for HT1376 is a little more complicated. Using freshly prepared RNA, this cell line tested negative for FoxP3 by PCR, and showed only marginal staining for FoxP3 by flow cytometry. However, RNA from this cell line that was prepared several years ago tested positive for both FoxP3 and ESO. It is possible that the expression of FoxP3 was lost with extended culture.

ESO expression after siRNA-mediated Foxp3 knockdown also is tested.

Thus far, it appears that all FoxP3-negative cell lines also lack ESO expression, although many FoxP3-positive cell lines also lack ESO expression. One could possibly make the case that FoxP3 is necessary but not sufficient for expression of ESO.

Example 8

FoxP3 Expression is Induced During EBV-Mediated B Cell Transformation in Vitro and In Vivo Infection of B cells with Epstein-Barr virus (EBV) induces transformation and can therefore serve as an in vitro model for B cell lymphoma formation. We used this model to investigate whether transformation is associated with de novo induction of FoxP3 expression. Peripheral blood mononuclear cells (PBMC) from 4 healthy donors were infected with EBV in vitro and cultured in the presence of cyclosporine to block the expansion of EBV-specific T cells. When analyzed by flow cytometry after 30 days' culture, a distinct population of cells with high forward and side scatter characteristics was evident, the majority of which expressed CD19 and MHC class II, corresponding to the transformed B cell blasts (FIG. 6*a*). In addition, a population of small lymphocytes remained, and while many of these were T cells, a fraction were $CD19^+$ and therefore likely represent resting B cells that have escaped transformation. This population was not evident in more established EBV-transformed B cell lines (not shown), suggesting that it is gradually diluted out with extensive passage.

Prior to culture, $CD19^+$ B cells did not express detectable FoxP3, as expected. After 30 days' culture, the small B cells still lacked FoxP3 expression whereas the transformed B cell blasts had clearly up-regulated FoxP3 expression (FIG. 6*b*). A more detailed time-course analysis (FIG. 6*c*) revealed that the blasts were first detectable at around day 15 of culture, at which time they had already begun to up-regulate FoxP3. With further culture, the level of FoxP3 expression progressively increased until the last day of analysis (day 30). In contrast, expression of FoxP3 in the small B cells remained low to undetectable throughout the culture period, arguing against a non-specific induction of FoxP3 in cultured B cells. After further expansion to generate larger cell numbers, expression of FOXP3 mRNA was confirmed for one of these cultures by RT-PCR (not shown).

Post-transplant lymphoproliferative disorder (PTLD) is a complication of solid organ and bone marrow transplantation in which B cell lymphomas develop following EBV-induced transformation of B cells (24). Given that transformation of B cells in vitro with EBV appeared to induce FoxP3 expression, we hypothesized that B cell lymphomas from PTLD patients would also express FoxP3. To test this, cryopreserved cell samples from a patient who developed PTLD following a heart transplant were assessed for FoxP3 expression (FIG. 6*d*). Normal $CD19^+$ B cells within the patient's PBMC did not express FoxP3, as expected. However, when disaggregated lymphoma tissue from the same patient was analyzed, a distinct population of $FoxP3^+$ $CD19^+$ B cells could be detected. These were clearly not Treg, as $CD4^+$ T cells were gated out of the analysis. Interestingly, the $FoxP3^+$ B cells expressed a lower level of CD19 than the $FoxP3^-$ B cells, although the significance of this observation is unclear at present.

Example 9

FoxP3-Expressing Tumor Cell Lines Suppress T Cell Proliferation

Considering the central role that FoxP3 plays in the development and function of Treg, we hypothesized that expression of FoxP3 by tumor cells may endow them with Treg-like activity, enabling them to suppress the generation of anti-tumor cytotoxic T cell (CTL) responses. To test this concept, $CD8^+$ T cells were purified from PBMC, labeled with CFSE and co-cultured with FoxP3-expressing tumor cells or freshly isolated Treg in the presence of a polyclonal stimulus to induce T cell proliferation (FIG. 7*a-b*). As expected, Treg induced a dose-dependent inhibition of T cell proliferation. Moreover, three out of four tumor cell lines tested (two melanoma lines and one breast cancer line) also significantly suppressed T cell proliferation. Of note, the suppression induced by tumor cell lines was generally even more potent than that induced by Treg; for example, SK-Mel-14 almost completely abolished T cell proliferation even at a tumor:T cell ratio of 2:1. Similar results were observed using $CD4^+$ T cell responders (not shown).

Figure 7:
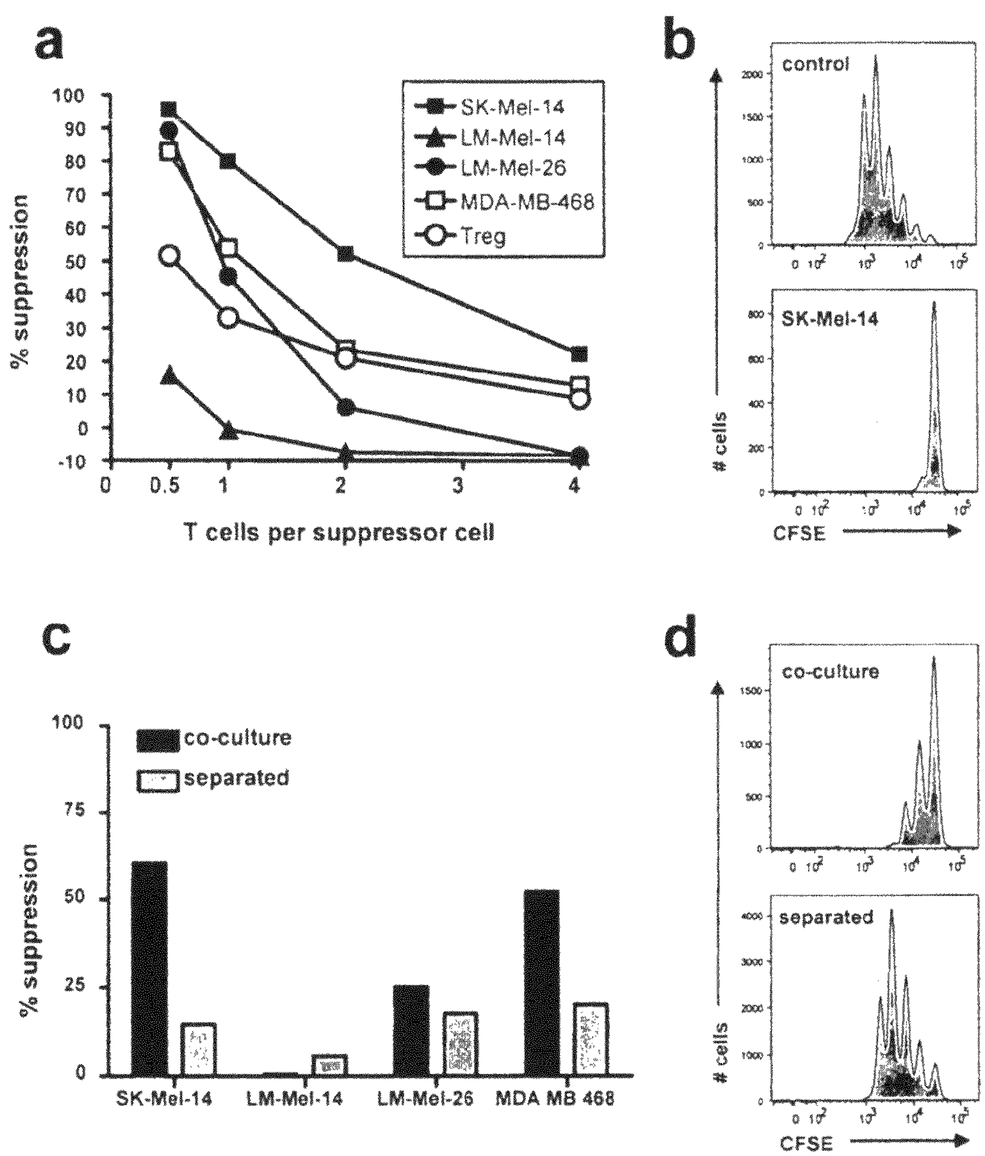
FIG. 7: FoxP3-expressing tumor cell lines suppress T cell proliferation. $CD8^+$ T cells were purified from PBMC of a healthy donor, labeled with CFSE and activated with antibody-coated beads for 4 days in the presence or absence of the indicated tumor cells or $CD4^+$ $CD25^+$ Treg (isolated from a different donor). The percent suppression value for each tumor cell/Treg co-culture was calculated relative to T cells cultured in the absence of suppressor cells, as described in Methods. In (a-b), T cells were cultured in 96-well plates with titrated numbers of tumor cells/Treg. In (c-d), tumor cells were placed in the bottom chamber of a 0.4 μm Transwell plate and T cells added to either the same chamber ('co-culture') or the upper chamber ('separated'). Flow cytometry profiles (b) and (c) show results for SK-Mel-14 at 2:1 tumor:T cell ratio. All data are representative of two independent experiments with similar results.

A characteristic feature of the suppression mediated by Treg is that it is dependent on close contact between Treg and the responding T cells (5). To test if this was also the case for tumor cells, duplicate cultures were set up in which the tumor cells and the responding T cells were either placed in the same well or were separated by a semi-permeable Transwell® membrane (FIG. 7*c-d*). The suppression mediated by SK-Mel-14 and MDA-MB-468 cell lines was clearly reduced when the tumor cells were physically separated from the responding T cells, indicating that the suppressive effect of these cells is primarily contact dependent. In contrast, the suppression mediated by LM-Mel-26 was only slightly affected by physical separation, suggesting that this cell line uses suppressive mechanisms that are not dependent on direct contact with the target cells, such as the production of immunosuppressive cytokines. In keeping with FIG. 7(*a*), LM-Mel-14 was not suppressive under either condition.

Example 10

FOXP3 Knockdown in Melanoma Cell Lines

Reagents

FOXP3 positive, HLA-A2, HLA-B7 and HLA-C3 positive melanoma cell lines are selected:

- HLA-A2+HLA-B7: LM-Mel-1a, LM-Mel-5, LM-Mel-26
- HLA-A2+HLA-C3: LM-Mel-19, LM-Mel-31, LM-Mel-33, LM-Mel-34
- HLA-C3 alone: LM-Mel-14, LM-Mel-28

FOXP3 siRNA plus relevant controls are obtained from commercial suppliers, such as Ambion (via Geneworks in Adelaide, Australia), IDT, and Dharmacon. FOXP3-AS2 antisense oligonucleotide can be obtained from MWG Biotech.

Lipofectamine/OptiMEM are used as transfection reagents.

Knockdown

Trial ~3× siRNA, compare to ubiquitous positive and scrambled negative controls.

Relative knockdown is measured by FACS, RT-PCR and Western analyses.

Effect of FOXP3 Knockdown on Melanoma Cell Line Growth

The following assays are run to observe the effects of FOXP3 knockdown:

- Proliferation by MTS assay
- Clonogenicity by CFU in agar
- Morphology and antigen expression by PCR and IHC
- CTAg and differentiation antigens
- Class I/II, GITR, proteasome components Immunological Consequences of FOXP3 Inhibition in Melanoma Cell Lines The immunological effects of FOXP3 knockdowns are assayed by:

- Cytokine release by FOXP3 knockdown melanoma cells, measured using a BD Cytometric Bead Array.
- Cytotoxicity, measured using calcein release assay, inhibition of clonogenicity, and CCIA.
- In vitro stimulation of CD4/CD8 T-cells by melanoma cells is measured by ICS for IFN-γ and T-cell proliferation by CFSE.
- Using melanoma antigen specific CD8 T-cells: CGW Melan-A 5-10% specific after one stimulation; A2, B7 and C3 restricted NY-ESO-1 specific T-cells; and EBV, FLU epitope controls.

In Vivo Immunological Consequences of FOXP3 Inhibition in Melanoma Cell Lines

An inducible shRNA transfection construct for FOXP3 is developed.

Tumourigenicity in mouse model is tested.

FOXP3 inhibition influence on tumour formation and immune response to adoptively transferred melanoma specific human CD8 T-cells is tested.

Effect of Drugs on FOXP3 Expression in Melanoma

If FOXP3 is immunologically or biologically relevant in melanoma cell lines, the effect of pharmacological manipulation of melanoma cell lines is assessed, as follows.

- In vitro: proliferation, clonogenicity, antigen expression as above.
- In vivo: tumourigenicity, and adoptively transferred immune response to melanoma xenografts in drug treated animals.

Examples of agents that may influence CD4+CD25+ FOXP3+ T-regs include:

a. Cyclophosphamide (Motoyoshi et al., Oncol Rep. 2006 July; 16(1):141-6.

b. IL-2 (Ahmadzadeh and Rosenberg, Blood. 2006 Mar. 15; 107(6):2409-14; Cesana et al, J Clin Oncol. 2006 Mar. 1; 24(7):1169-77.)

c. Interferon (Putheti, J Clin Immunol. 2004 March; 24(2): 155-61.)

d. Mycophenlate mofetil, 1,25-vitamin-D3 (Gregori, J Immunol. 2001 Aug. 15; 167(4):1945-53.)

e. Fludarabine (Beyer et al, Blood. 2005 Sep. 15; 106(6): 2018-25.)

Example 11

Figure 11:
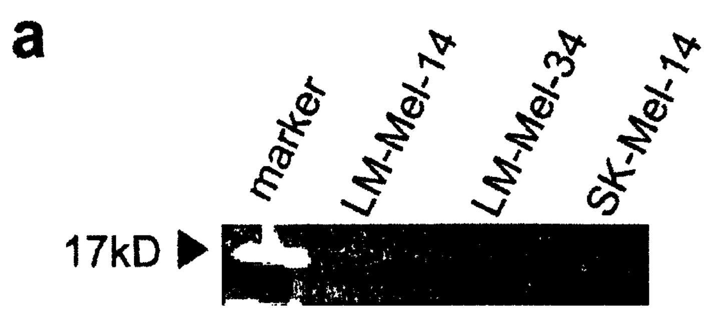
FIG. 11: Western blotting of melanoma cell line lysates using an antibody raised against the Δ3,4 variant. A polyclonal antiserum to a 15 amino acid variant FoxP3 peptide (SSRERWYSLWSSSWC; SEQ ID NO:13) was used at a final concentration of 2 μg/ml to probe lysates prepared from three different melanoma cell lines, all of which express the Δ3,4 FoxP3 variant by RT-PCR (the Δ3,4 FoxP3 variant is also referred to as the Δ2,3 FoxP3 variant herein). Note that the predicted molecular weight of the variant is approximately 17 kD.
Figure 11:
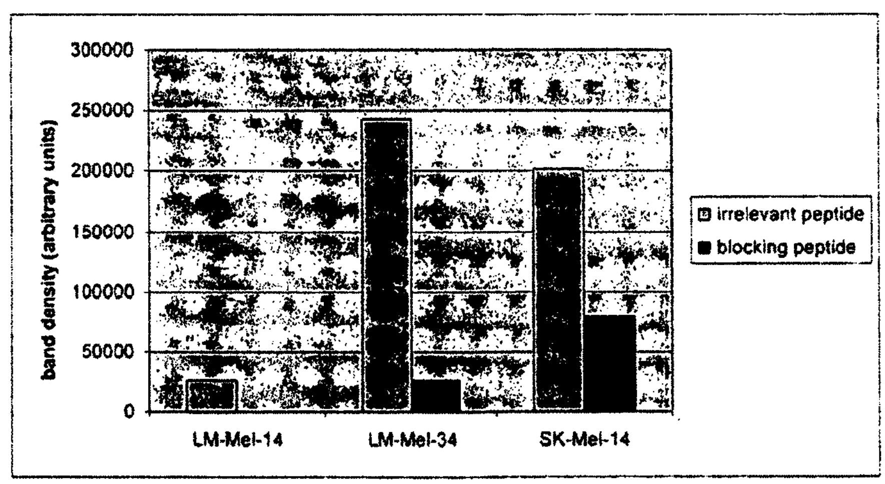

Western Blotting of Melanoma Cell Line Lysates Using an Antibody Raised Against the Δ3,4 Variant A 15 amino acid peptide (SSRERWYSLWSSSWC; SEQ ID NO:13) was synthesized corresponding to a region of the frame-shifted portion of the variant FoxP3 polypeptide (which bears no similarity to wild-type FoxP3). This peptide was conjugated to the carrier KLH (keyhole limpet hemocyanin) and used to immunize rabbits, and IgG was purified from the immune serum by Protein A chromatography. This antiserum was used at a final concentration of 2 μg/ml to probe lysates prepared from three different melanoma cell lines, all of which express the Δ3,4 FoxP3 variant by RT-PCR. Note that the predicted molecular weight of the variant is approximately 17 kD. FIG. 11*a* demonstrates the presence of a band of the expected size for all three melanoma cell lines tested.

To demonstrate the specificity of the reaction, the antibody was pre-blocked for 2 hours at room temperature with either the peptide used for immunization or an irrelevant peptide control (0.2 μg/ml). The antibody/peptide mixture was then used for Western blotting and band density was determined using ImageQuaNT software. This analysis is shown in FIG. 11*b*, and demonstrates that the band intensity is greatly reduced after blocking with the specific peptide.

Example 12

T Cell Responses to the Δ3,4 Variant in a Patient with Advanced Melanoma

Figure 12:
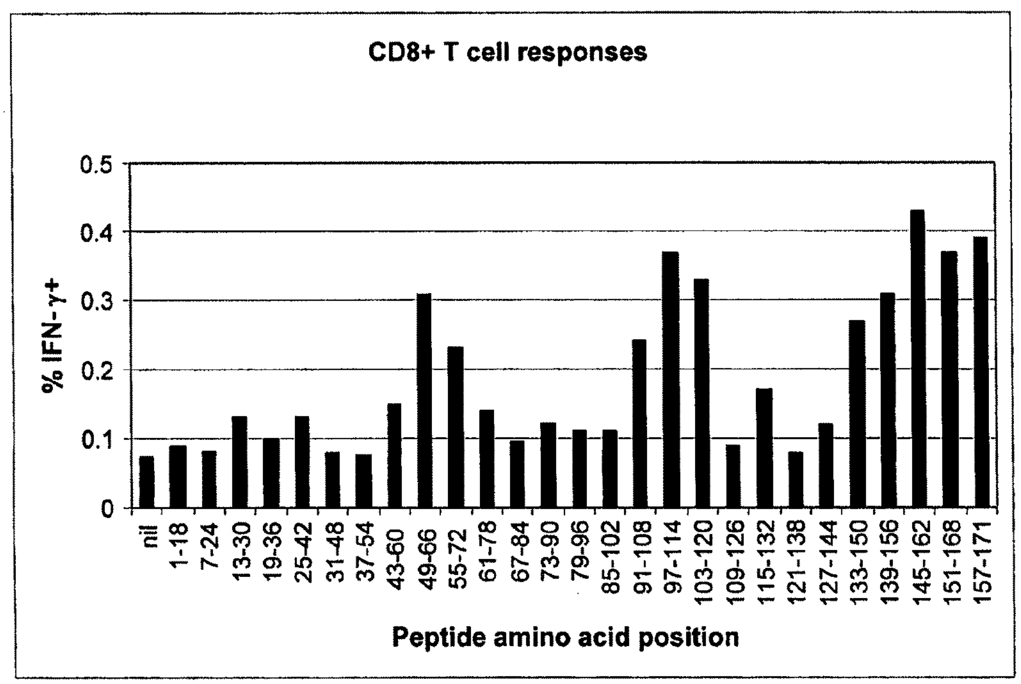
FIG. 12: T cell responses to the Δ3,4 variant in a patient with advanced melanoma. A panel of overlapping 18 amino acid peptides was synthesized covering the entire predicted protein sequence of the Δ3,4 variant. Patient peripheral blood mononuclear cells (PBMC) were cultured with each peptide for 11 days in the presence of 25 IU/ml IL-2 and then re-stimulated with the same peptide for 4 hours in the presence of Brefeldin-A. The cells were then stained with fluorochrome-conjugated antibodies to CD4 and CD8, fixed with 1% formaldehyde and incubated overnight with FITC-conjugated anti-IFN-γ in the presence of 0.2% saponin. Cells were then subject to flow cytometric analysis, gating on either $CD8^+$ (FIG. 12*a*) or $CD4^+$ (FIG. 12*b*) T cells.
Figure 12:
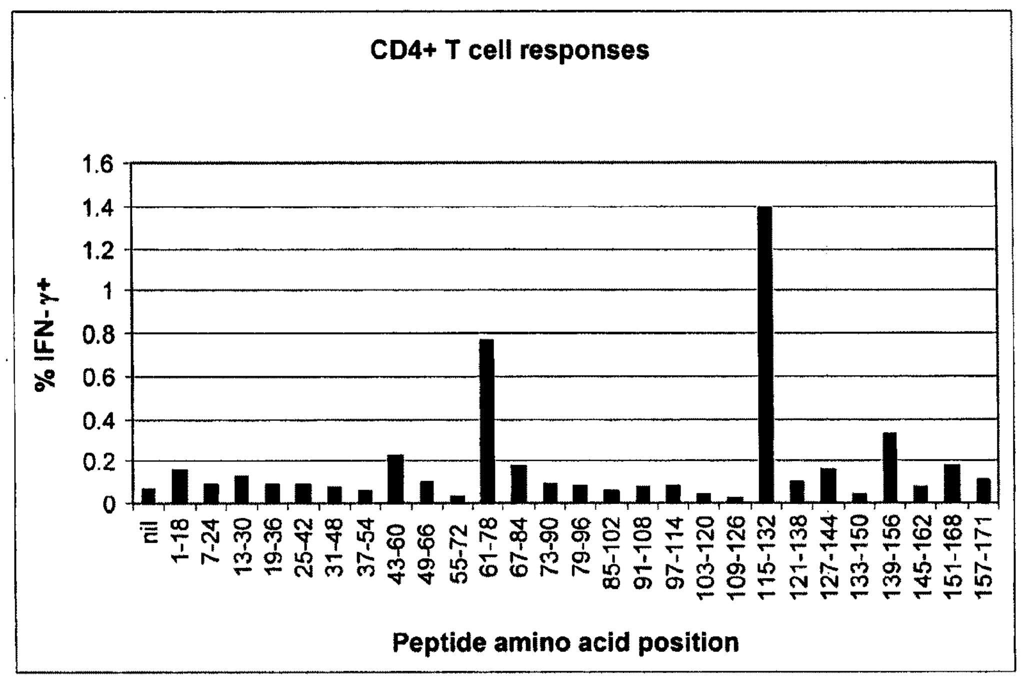

A panel of overlapping 18 amino acid peptides was synthesized covering the entire predicted protein sequence of the Δ3,4 variant. Patient peripheral blood mononuclear cells (PBMC) were cultured with each peptide for 11 days in the presence of 25 IU/ml IL-2 and then re-stimulated with the same peptide for 4 hours in the presence of Brefeldin-A (see Jackson et al, J. Immunol. Methods. 291: 51-62). The cells were then stained with fluorochrome-conjugated antibodies to CD4 and CD8, fixed with 1% formaldehyde and incubated overnight with FITC-conjugated anti-IFN-γ in the presence of 0.2% saponin. Cells were then subject to flow cytometric analysis, gating on either $CD8^+$ (FIG. 12*a*) or $CD4^+$ (FIG. 12*b*) T cells.

Discussion

Figure 5:
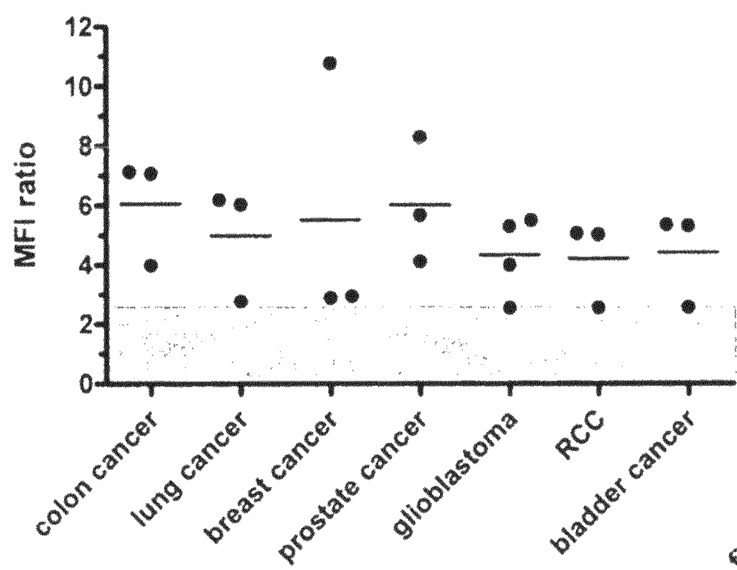
FIG. 5: Expression of FoxP3 in cell lines derived from other types of solid tumor or normal fibroblasts. (a-b): tumor cell lines (a) and normal fibroblast cultures (early and late passage; b) were analysed by flow cytometry. The mean fluorescence intensity (MFI) was determined following staining with anti-FoxP3 and isotype control and the ratio calculated. The grey region indicates the background level as determined in FIG. 3*b*. (c): RNA extracted from $1\times10^6$ cells was reverse transcribed and the cDNA amplified by PCR (35 cycles) using primers specific for FOXP3 and CYP-A. Shown are representative cell lines derived from the following types of cancer: colon cancer (CaCo2), lung cancer (NCI-H460), breast cancer (MDA-MB-468), prostate cancer (PC3), glioblastoma (A172), renal cell carcinoma (SKRC09) and bladder cancer (5637); as well as CD4+ T cells and NK cells purified from peripheral blood.
Figure 5:
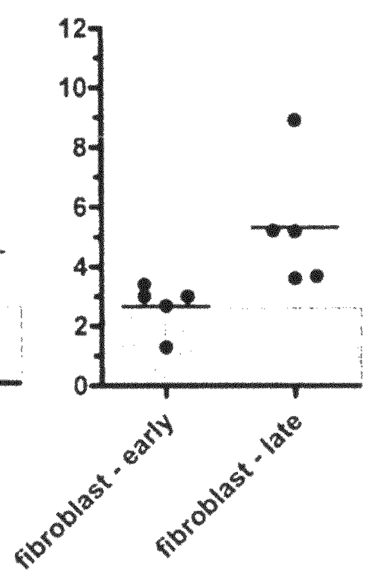
Figure 5:
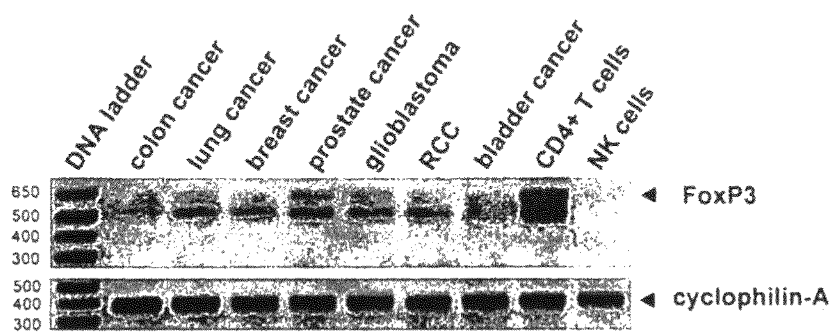

Using a wide variety of approaches, the present study demonstrates, using a variety of approaches, that the FoxP3 transcription factor is expressed by melanoma cells, virally-transformed B cells and cell lines derived from a variety of solid tumors. This observation is particularly interesting as it was previously believed that FoxP3 expression was strictly limited to T cells (19, 20). A study by Chang et al in 2005 had originally suggested that FoxP3 was also expressed by thymic epithelium in the mouse (25), but this has since been shown not to be the case (26). A recent report demonstrated that FOXP3 is a tumor suppressor gene in both mouse and human breast cancer (27). The authors detected expression of FoxP3 protein in normal breast epithelium, and showed that expression was lost or reduced in breast cancer due to reduced levels of FOXP3 transcription or deletion of the FOXP3 locus. As a result, FoxP3-mediated repression of the HER-2/ErbB2 oncogene is lifted, which is likely to be an important contributing factor to carcinogenesis. Interestingly, the authors also detected novel FOXP3 splice variants in breast cancer cells. One of these is referred to as lacking exons 3 and 4, resulting in a frame-shift beginning at codon 70 and an early termination codon at codon 172. This frame-shift is identical to that which we predicted from our Δ2,3 isoform, and it appears that these variants are in fact the same, despite the different designations (Δ2,3 versus Δ3,4). It appears that this discrepancy has arisen because Zuo et al consider the 5' UTR as exon 1, whereas we have followed the convention in the FoxP3 literature (11, 14, 15, 23) to consider the first translated region as exon 1. Nevertheless, it appears that this splice variant is expressed in a wide range of cancers including melanoma (FIG. 4), breast cancer (FIG. 4, and reference (27)) and others (FIG. 5).

In contrast to breast cancer, our results suggest that melanoma is characterized by up-regulation of FoxP3 rather than down-regulation. First, FoxP3 expression was expressed at readily detectable levels by the majority of melanoma cell lines, in contrast to breast cancer cell lines which frequently lacked FoxP3 expression (reference (27), and FIG. 5). In addition, normal epidermal melanocytes lacked significant FoxP3 expression but the malignant counterpart (melanoma cells) clearly expressed FoxP3. Normal breast epithelium, in contrast, expresses FoxP3 constitutively and expression is lost or down-regulated in breast cancer tissue.

Recent studies into the epigenetic regulation of FOXP3 have revealed that gene expression is normally repressed by methylation of a CpG-rich element in the 5'-UTR. In Tregs, however, this region is almost completely demethylated, leading to stable, heritable FOXP3 gene expression (28). The importance of such epigenetic control is revealed following treatment of NK cells with the demethylating agent 5-aza-2' deoxycytidine, which allows these cells to abnormally express FoxP3 in response to IL-2 (29). Interestingly, aberrant methylation and demethylation are common events in melanoma, and many melanoma antigens, including the MAGE and cancer testis (CT) antigen families, are expressed following promoter demethylation (30, 31). Together, these observations raise the possibility that deregulated demethylase activity in melanoma cells results in the coordinate induction of tumor antigen and FoxP3 expression.

Given the established role for FoxP3 in directing Treg activity, up-regulated FoxP3 expression in melanoma cells may endow them with Treg-like activity and enable FoxP3+ melanoma cells to resist immune attack. In support of this hypothesis, FoxP3-expressing melanoma cells could effectively suppress T cell proliferation, with almost complete inhibition being observed when melanoma cells outnumber T cells 2:1, a situation that is very likely to occur within the tumor microenvironment. Interestingly, the single FoxP3+ breast cancer cell line we could identify was also strongly suppressive.

Tumor cells are well known to have immunosuppressive activity. These activities include production of immunoregulatory cytokines, prevention of DC maturation, generation of Treg, and many others (6, 32, 33). However, until now, very few studies have shown a direct effect of tumor cells on inhibiting T cell activation and expansion (34). Our results show that the ability to suppress T cell proliferation is common amongst FoxP3-expressing tumor cell lines. In keeping with our results, Hinz et al (42) found that FoxP3+ pancreatic carcinoma cell lines could also suppress T cell proliferation. Importantly, these authors also used an RNA interference approach to demonstrate that FoxP3 was at least partially responsible for the suppression mediated by tumor cells. Interestingly, however, we have observed that some tumor cell lines expressing only borderline levels of FoxP3 could also effectively suppress T cell proliferation (data not shown), supporting the view that tumor cells possess additional immunosuppressive mechanisms that are independent of FoxP3. In future studies, it will be important to directly assess what contribution FoxP3 makes to the observed immunosuppressive activity of tumor cells; for example, by using RNAi approaches.

The function of FoxP3 in cancer may depend on the nature of the tumor. In breast cancer, loss of FoxP3 expression is thought to contribute to tumorigenesis by allowing enhanced expression of the HER-2/ErbB2 oncogene, which plays a key role in breast cancer progression (27). In this situation, it is likely that FoxP3 expression would be expected to be selected against, as any immune-suppressive advantage FoxP3 expression could confer will be outweighed by the benefit of up-regulated expression of a relevant oncogene. In keeping with this concept, we found only one out of three breast cancer cell lines to be FoxP3+. In contrast, the HER-2/ErbB2 oncogene is not reported to be involved in the pathogenesis of melanoma (35) and therefore there would be no reason for FoxP3 expression to be selected against; to the contrary, induction of FoxP3 expression may provide a survival advantage to melanoma cells by endowing them with Treg-like activity. An important question for future studies will be to determine if FoxP3 expression correlates with disease progression or has prognostic significance.

In addition to solid tumors, we have provided evidence that B cell lymphomas can also aberrantly express FoxP3. Transformation of normal B cells with the oncogenic virus EBV induced FoxP3 expression, and a sub-population of B lymphoma cells from a PTLD patient were $FoxP3^{+}$. For several years, it has been recognized that adult T cell leukemia/lymphoma is frequently associated with FoxP3 expression (36). The common interpretation of this observation is that these malignancies are derived from the Treg lineage. However, our observation of de novo FoxP3 induction in malignant B cells raises the possibility that a proportion of $FoxP3^{+}$ T cell leukemias are in fact derived from non-regulatory T cells that have begun expressing FoxP3 during tumorigenesis.

Our data raise the possibility that FoxP3 may be a potential tumor antigen that can be targeted by vaccination. Although FoxP3 is a self antigen, it is not expressed in thymic epithelium (26) and tolerance to this antigen is apparently very limited, as T cell responses against FoxP3 could be readily induced following vaccination of mice (37). A potential concern in targeting FoxP3 as a tumor antigen is the possibility that Treg would also be targeted for destruction, potentially leading to autoimmunity. Of note, however, is our observation that a number of tumor cell lines expressed a FOXP3 mRNA isoform lacking exons 2 and 3 which was not detectable in Treg. This isoform is predicted to encode a novel protein which is approximately half the size of FoxP3 and—due to a translation frame-shift—includes a 103aa sequence that has very limited homology to FOXP3 any other known protein sequence. Targeting this protein by vaccination would allow the generation of T cells that recognize tumor but not Treg, thereby eliminating the possibility of autoimmune complications. Interestingly, Zuo et al also detected novel FOXP3 mRNA variants in breast cancer cells, one of which appears to be identical to the Δ2,3 variant (although these authors refer to this variant as Δ 3,4; presumably because they consider the 5' UTR as exon 1). Therefore, alternative splicing of the FOXP3 gene appears to be a common theme in cancer.

This study demonstrates, for the first time, that FoxP3 is expressed in melanoma cells both directly ex vivo and after culture in vitro. Thus, FoxP3 expression by melanoma cells is neither a culture artifact nor a transient phenomenon. We have also demonstrated FoxP3 expression in B cells that have been transformed with EBV in vitro and in vivo, as well as a variety of other tumor cell lines, although further investigation is required to determine if each of these tumors also expresses FoxP3 in vivo. These observations suggest a re-interpretation of previous studies in which Treg prevalence in tumors was investigated by measuring FOXP3 transcripts in the tumor tissue, as some of these transcripts may have originated from the tumor cells themselves, not from Treg. Clearly, FoxP3 expression and function can no longer be considered to be restricted to the T cell lineage—but may instead play a wider role in biology; for example, by endowing tumor cells with immune suppressive activity. These observations raise the possibility of enhancing tumor immunogenicity by knocking down FoxP3 expression (for example, using RNA interference) or, alternatively, by vaccinating against the FoxP3 Δ2,3 isoform.

Western blotting and T cell screening data confirm that the FoxP3 Δ2,3 isoform is expressed and a suitable target for immunological therapeutic intervention. Western blot data demonstrated expression of the FoxP3 Δ2,3 isoform using a polyclonal antibody raised against the frame-shifted region. Results from screening a patient for T cells specific for the FoxP3 Δ2,3 isoform also indicate that the FoxP3 Δ2,3 isoform is expressed and generates a CD4+ and CD8+ T cell immune response. A series of overlapping peptides were synthesized covering the entire sequence of the variant and were used to stimulate patient PBMC. It is interesting to note that no responses were detected in the first 70 amino acids of the protein, which is the portion encoded by exon 1 and is identical to native FoxP3. In contrast, the region between amino acids 97-171 appeared to have many epitopes. This is the portion of the protein generated from the alternative reading frame, and has a completely different sequence as compared to FoxP3. These results support the concept that this variant can act as a tumour antigen, and also provide indirect evidence that the variant is produced as a protein, as otherwise it would not be possible to generate an immune response to it.

REFERENCES

1. Sakaguchi, S. 2004. Naturally arising CD4+ regulatory t cells for immunologic self-tolerance and negative control of immune responses. *Annu Rev Immunol* 22:531-562.
2. Mills, K. H., and McGuirk, P. 2004. Antigen-specific regulatory T cells—their induction and role in infection. *Semin Immunol* 16:107-117.
3. Zwar, T. D., van Driel, I. R., and Gleeson, P. A. 2006. Guarding the immune system: suppression of autoimmunity by CD4+CD25+ immunoregulatory T cells. *Immunol Cell Biol* 84:487-501.
4. Fontenot, J. D., and Rudensky, A. Y. 2005. A well adapted regulatory contrivance: regulatory T cell development and the forkhead family transcription factor Foxp3. *Nat Immunol* 6:331-337.

5. Miyara, M., and Sakaguchi, S. 2007. Natural regulatory T cells: mechanisms of suppression. *Trends Mol Med* 13:108-116.
6. Zou, W. 2006. Regulatory T cells, tumour immunity and immunotherapy. *Nat Rev Immunol* 6:295-307.
7. Beyer, M., and Schultze, J. L. 2006. Regulatory T cells in cancer. *Blood* 108:804-811.
8. Curiel, T. J., Coukos, G., Zou, L., Alvarez, X., Cheng, P., Mottram, P., Evdemon-Hogan, M., Conejo-Garcia, J. R., Zhang, L., Burow, M., et al. 2004. Specific recruitment of regulatory T cells in ovarian carcinoma fosters immune privilege and predicts reduced survival. *Nat Med* 10:942-949.
9. Mourmouras, V., Fimiani, M., Rubegni, P., Epistolato, M. C., Malagnino, V., Cardone, C., Cosci, E., Nisi, M. C., and Miracco, C. 2007. Evaluation of tumour-infiltrating CD4+ CD25+FOXP3+ regulatory T cells in human cutaneous benign and atypical naevi, melanomas and melanoma metastases. *Br J Dermatol* 157:531-539.
10. Viguier, M., Lemaitre, F., Verola, O., Cho, M. S., Gorochov, G., Dubertret, L., Bachelez, H., Kourilsky, P., and Ferradini, L. 2004. Foxp3 expressing CD4+CD25(high) regulatory T cells are overrepresented in human metastatic melanoma lymph nodes and inhibit the function of infiltrating T cells. *J Immunol* 173:1444-1453.
11. Ziegler, S. F. 2006. FOXP3: of mice and men. *Annu Rev Immunol* 24:209-226.
12. Bennett, C. L., Christie, J., Ramsdell, F., Brunkow, M. E., Ferguson, P. J., Whitesell, L., Kelly, T. E., Saulsbury, F. T., Chance, P. F., and Ochs, H. D. 2001. The immune dysregulation, polyendocrinopathy, enteropathy, X-linked syndrome (IPEX) is caused by mutations of FOXP3. *Nat Genet.* 27:20-21.
13. Bacchetta, R., Passerini, L., Gambineri, E., Dai, M., Allan, S. E., Perroni, L., Dagna-Bricarelli, F., Sartirana, C., Matthes-Martin, S., Lawitschka, A., et al. 2006. Defective regulatory and effector T cell functions in patients with FOXP3 mutations. *J Clin Invest* 116:1713-1722.
14. Yagi, H., Nomura, T., Nakamura, K., Yamazaki, S., Kitawaki, T., Hori, S., Maeda, M., Onodera, M., Uchiyama, T., Fujii, S., et al. 2004. Crucial role of FOXP3 in the development and function of human CD25+CD4+ regulatory T cells. *Int Immunol* 16:1643-1656.
15. Allan, S. E., Passerini, L., Bacchetta, R., Crellin, N., Dai, M., Orban, P. C., Ziegler, S. F., Roncarolo, M. G., and Levings, M. K. 2005. The role of 2 FOXP3 isoforms in the generation of human CD4+ Tregs. *J Clin Invest* 115:3276-3284.
16. Gavin, M. A., Torgerson, T. R., Houston, E., DeRoos, P., Ho, W. Y., Stray-Pedersen, A., Ocheltree, E. L., Greenberg, P. D., Ochs, H. D., and Rudensky, A. Y. 2006. Single-cell analysis of normal and FOXP3-mutant human T cells: FOXP3 expression without regulatory T cell development. *Proc Natl Acad Sci USA* 103:6659-6664.
17. Pillai, V., Ortega, S. B., Wang, C. K., and Karandikar, N. J. 2007. Transient regulatory T-cells: a state attained by all activated human T-cells. *Clin Immunol* 123:18-29.
18. Walker, M. R., Kasprowicz, D. J., Gersuk, V. H., Benard, A., Van Landeghen, M., Buckner, J. H., and Ziegler, S. F. 2003. Induction of FoxP3 and acquisition of T regulatory activity by stimulated human CD4+CD25− T cells. *J Clin Invest* 112:1437-1443.
19. Brunkow, M. E., Jeffery, E. W., Hjerrild, K. A., Paeper, B., Clark, L. B., Yasayko, S. A., Wilkinson, J. E., Galas, D., Ziegler, S. F., and Ramsdell, F. 2001. Disruption of a new forkhead/winged-helix protein, scurfin, results in the fatal lymphoproliferative disorder of the scurfy mouse. *Nat Genet* 27:68-73.
20. Fontenot, J. D., Rasmussen, J. P., Williams, L. M., Dooley, J. L., Farr, A. G., and Rudensky, A. Y. 2005. Regulatory T cell lineage specification by the forkhead transcription factor foxp 3. *Immunity* 22:329-341.
21. Busam, K. J., and Jungbluth, A. A. 1999. Melan-A, a new melanocytic differentiation marker. *Adv Anat Pathol* 6:12-18.
22. Pluschke, G., Vanek, M., Evans, A., Dittmar, T., Schmid, P., Itin, P., Filardo, E. J., and Reisfeld, R. A. 1996. Molecular cloning of a human melanoma-associated chondroitin sulfate proteoglycan. *Proc Natl Acad Sci USA* 93:9710-9715.
23. Smith, E. L., Finney, H. M., Nesbitt, A. M., Ramsdell, F., and Robinson, M. K. 2006. Splice variants of human FOXP3 are functional inhibitors of human CD4+ T-cell activation. *Immunology* 119:203-211.
24. Davis, J. E., and Moss, D. J. 2004. Treatment options for post-transplant lymphoproliferative disorder and other Epstein-Barr virus-associated malignancies. *Tissue Antigens* 63:285-292.
25. Chang, X., Gao, J. X., Jiang, Q., Wen, J., Seifers, N., Su, L., Godfrey, V. L., Zuo, T., Zheng, P., and Liu, Y. 2005. The Scurfy mutation of FoxP3 in the thymus stroma leads to defective thymopoiesis. *J Exp Med* 202:1141-1151.
26. Liston, A., Farr, A. G., Chen, Z., Benoist, C., Mathis, D., Manley, N. R., and Rudensky, A. Y. 2007. Lack of Foxp3 function and expression in the thymic epithelium. *J Exp Med* 204:475-480.
27. Zuo, T., Wang, L., Morrison, C., Chang, X., Zhang, H., Li, W., Liu, Y., Wang, Y., Liu, X., Chan, M. W., et al. 2007. FOXP3 is an X-linked breast cancer suppressor gene and an important repressor of the HER-2/ErbB2 oncogene. *Cell* 129:1275-1286.
28. Baron, U., Floess, S., Wieczorek, G., Baumann, K., Grutzkau, A., Dong, J., Thiel, A., Boeld, T. J., Hoffmann, P., Edinger, M., et al. 2007. DNA demethylation in the human FOXP3 locus discriminates regulatory T cells from activated FOXP3(+) conventional T cells. *Eur J Immunol* 37:2378-2389.
29. Zom, E., Nelson, E. A., Mohseni, M., Porcheray, F., Kim, H., Litsa, D., Bellucci, R., Raderschall, E., Canning, C., Soiffer, R. J., et al. 2006. IL-2 regulates FOXP3 expression in human CD4+CD25+ regulatory T cells through a STAT-dependent mechanism and induces the expansion of these cells in vivo. *Blood* 108:1571-1579.
30. De Smet, C., De Backer, O., Faraoni, I., Lurquin, C., Brasseur, F., and Boon, T. 1996. The activation of human gene MAGE-1 in tumor cells is correlated with genome-wide demethylation. *Proc Natl Acad Sci USA* 93:7149-7153.
31. Nicholaou, T., Ebert, L., Davis, I. D., Robson, N., Klein, O., Maraskovsky, E., Chen, W., and Cebon, J. 2006. Directions in the immune targeting of cancer: lessons learned from the cancer-testis Ag NY-ESO-1. *Immunol Cell Biol* 84:303-317.
32. Drake, C. G., Jaffee, E., and Pardoll, D. M. 2006. Mechanisms of immune evasion by tumors. *Adv Immunol* 90:51-81.
33. Zou, W. 2005. Immunosuppressive networks in the tumour environment and their therapeutic relevance. *Nat Rev Cancer* 5:263-274.
34. Huber, D., Philipp, J., and Fontana, A. 1992. Protease inhibitors interfere with the transforming growth factor-beta-dependent but not the transforming growth factorbeta-independent pathway of tumor cell-mediated immunosuppression. *J Immunol* 148:277-284.

35. Inman, J. L., Kute, T., White, W., Pettenati, M., and Levine, E. A. 2003. Absence of HER2 overexpression in metastatic malignant melanoma. *J Surg Oncol* 84:82-88.

36. Karube, K., Ohshima, K., Tsuchiya, T., Yamaguchi, T., Kawano, R., Suzumiya, J., Utsunomiya, A., Harada, M., and Kikuchi, M. 2004. Expression of FoxP3, a key molecule in CD4CD25 regulatory T cells, in adult T-cell leukaemia/lymphoma cells. *Br J Haematol* 126:81-84.

37. Nair, S., Boczkowski, D., Fassnacht, M., Pisetsky, D., and Gilboa, E. 2007. Vaccination against the forkhead family transcription factor Foxp3 enhances tumor immunity. *Cancer Res* 67:371-380.

38. Allan S E, Passerini L, Bacchetta R, et al. The role of 2 FOXP3 isoforms in the generation of human CD4+Tregs. J Clin Invest 2005; 115(11):3276-84.

39. Yagi H, Nomura T, Nakamura K, et al. Crucial role of FOXP3 in the development and function of human CD25+ CD4+ regulatory T cells. Int Immunol 2004; 16(11):1643-56.

40. Ziegler SF. FOXP3: of mice and men. Annu Rev Immunol 2006; 24:209-26.

41. Barrow, C., Browning, J., MacGregor, D., et al. Tumor antigen expression in melanoma varies according to antigen and stage. Clin Cancer Res, 12: 764-771, 2006.

42. Hinz, S., Pagerols-Raluy, L., Oberg, H. H., et al. Foxp3 expression in pancreatic carcinoma cells as a novel mechanism of immune evasion in cancer. Cancer Res, 67: 8344-8350, 2007.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. An isolated nucleic acid molecule selected from the group consisting of:

(a) isolated nucleic acid molecules comprising a nucleotide sequence that is at least 90% identical to the full length of a nucleotide sequence set forth as SEQ ID NO:6, foxp3 (SEQ ID NO:1) lacking exons 2 and 3, or foxp3 exons 1 and 4 joined together, or a full-length complement thereof; and (b) nucleic acid molecules fully encoding the same amino acid sequences as proteins fully encoded by (a) and that only differ from the nucleic acid molecules of (a) in codon sequence due to the degeneracy of the genetic code.

2. A composition comprising the isolated nucleic acid molecule of claim 1 and a carrier.

3. A composition comprising the isolated nucleic acid molecule of claim 1 attached to a solid substrate.

4. An expression vector comprising the isolated nucleic acid molecule of claim 1 operably linked to a promoter.

5. An isolated host cell transformed or transfected with the expression vector of claim 4.

* * * * *

UNITED STATES PATENT AND TRADEMARK OFFICE

CERTIFICATE OF CORRECTION

PATENT NO. : 8,420,791 B2
APPLICATION NO. : 12/312472
DATED : April 16, 2013
INVENTOR(S) : Ebert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 705 days.

Signed and Sealed this
Eighth Day of September, 2015

Michelle K. Lee

Michelle K. Lee
*Director of the United States Patent and Trademark Office*

SEQUENCE LISTING

```
<160> NUMBER OF SEQ ID NOS: 13

<210> SEQ ID NO 1
<211> LENGTH: 1869
<212> TYPE: DNA
<213> ORGANISM: Homo sapiens

<400> SEQUENCE: 1

gcacacactc atcgaaaaaa atttggatta ttagaagaga gaggtctgcg gcttccacac      60

cgtacagcgt ggtttttctt ctcggtataa aagcaaagtt gtttttgata cgtgacagtt     120

tcccacaagc caggctgatc cttttctgtc agtccacttc accaagcctg cccttggaca     180

aggacccgat gcccaacccc aggcctggca agccctcggc cccttccttg gcccttggcc     240

catccccagg agcctcgccc agctggaggg ctgcacccaa agcctcagac ctgctggggg     300

cccggggccc agggggaacc ttccagggcc gagatcttcg aggcggggcc catgcctcct     360

cttcttcctt gaaccccatg ccaccatcgc agctgcagct gcccacactg cccctagtca     420

tggtggcacc ctccggggca cggctgggcc ccttgcccca cttacaggca ctcctccagg     480

acaggccaca tttcatgcac cagctctcaa cggtggatgc ccacgcccgg acccctgtgc     540

tgcaggtgca ccccctggag agcccagcca tgatcagcct cacaccaccc accaccgcca     600

ctggggtctt ctccctcaag gcccggcctg gcctcccacc tgggatcaac gtggccagcc     660

tggaatgggt gtccagggag ccggcactgc tctgcacctt cccaaatccc agtgcaccca     720

ggaaggacag caccctttcg gctgtgcccc agagctccta cccactgctg gcaaatggtg     780

tctgcaagtg gcccggatgt gagaaggtct tcgaagagcc agaggacttc ctcaagcact     840

gccaggcgga ccatcttctg gatgagaagg gcagggcaca atgtctcctc cagagagaga     900

tggtacagtc tctggagcag cagctggtgc tggagaagga gaagctgagt gccatgcagg     960

cccacctggc tgggaaaatg gcactgacca aggcttcatc tgtggcatca tccgacaagg    1020

gctcctgctg catcgtagct gctggcagcc aaggccctgt cgtcccagcc tggtctggcc    1080

cccgggaggc ccctgacagc ctgtttgctg tccggaggca cctgtggggt agccatggaa    1140

acagcacatt cccagagttc ctccacaaca tggactactt caagttccac aacatgcgac    1200

ccccttcac ctacgccacg ctcatccgct gggccatcct ggaggctcca gagaagcagc     1260
```

```
ggacactcaa tgagatctac cactggttca cacgcatgtt tgccttcttc agaaaccatc   1320

ctgccacctg gaagaacgcc atccgccaca acctgagtct gcacaagtgc tttgtgcggg   1380

tggagagcga gaagggggct gtgtggaccg tggatgagct ggagttccgc aagaaacgga   1440

gccagaggcc cagcaggtgt tccaacccta cacctggccc ctgacctcaa gatcaaggaa   1500

aggaggatgg acgaacaggg gccaaactgg tgggaggcag aggtggtggg ggcagggatg   1560

ataggccctg gatgtgccca cagggaccaa gaagtgaggt ttccactgtc ttgcctgcca   1620

gggcccctgt tcccccgctg gcagccaccc cctcccccat catatccttt gccccaaggc   1680

tgctcagagg ggcccgggtc ctggccccag cccccacctc cgccccagac acacccccca   1740

gtcgagccct gcagccaaac agagccttca caaccagcca cacagagcct gcctcagctg   1800

ctcgcacaga ttacttcagg gctggaaaag tcacacagac acacaaaatg tcacaatcct   1860

gtccctcac                                                           1869
```

<210> SEQ ID NO 2
<211> LENGTH: 22
<212> TYPE: DNA
<213> ORGANISM: Homo sapiens

<400> SEQUENCE: 2

```
gcccttggac aaggacccga tg                                              22
```

<210> SEQ ID NO 3
<211> LENGTH: 22
<212> TYPE: DNA
<213> ORGANISM: Homo sapiens

<400> SEQUENCE: 3

```
catttgccag cagtgggtag ga                                              22
```

<210> SEQ ID NO 4
<211> LENGTH: 608
<212> TYPE: DNA
<213> ORGANISM: Homo sapiens

<400> SEQUENCE: 4

```
gcccttggac aaggacccga tgcccaaccc caggcctggc aagccctcgg ccccttcctt     60

ggcccttggc ccatccccag gagcctcgcc cagctggagg gctgcaccca aagcctcaga    120

cctgctgggg gcccggggcc caggggggaac cttccagggc cgagatcttc gaggcggggc    180

ccatgcctcc tcttcttcct tgaaccccat gccaccatcg cagctgcagc tgcccacact    240

gcccctagtc atggtggcac cctccggggc acggctgggc cccttgcccc acttacaggc    300

actcctccag gacaggccac atttcatgca ccagctctca acggtggatg cccacgcccg    360

gacccctgtg ctgcaggtgc accccctgga gagcccagcc atgatcagcc tcacaccacc    420

caccaccgcc actggggtct tctccctcaa ggcccggcct ggcctcccac ctgggatcaa    480

cgtggccagc ctggaatggg tgtccaggga gccggcactg ctctgcacct tcccaaatcc    540

cagtgcaccc aggaaggaca gcaccctttc ggctgtgccc cagagctcct acccactgct    600

ggcaaatg                                                             608
```

<210> SEQ ID NO 5
<211> LENGTH: 503
<212> TYPE: DNA
<213> ORGANISM: Homo sapiens

<400> SEQUENCE: 5

```
gcccttggac aaggacccga tgcccaaccc caggcctggc aagccctcgg ccccttcctt     60

ggcccttggc ccatccccag gagcctcgcc cagctggagg gctgcaccca aagcctcaga    120

cctgctgggg gcccggggcc caggggggaac cttccagggc cgagatcttc gaggcggggc   180

ccatgcctcc tcttcttcct tgaaccccat gccaccatcg cagctgcagc tctcaacggt    240

ggatgcccac gcccggaccc ctgtgctgca ggtgcacccc ctggagagcc cagccatgat    300

cagcctcaca ccacccacca ccgccactgg ggtcttctcc ctcaaggccc ggcctggcct    360

cccacctggg atcaacgtgg ccagcctgga atgggtgtcc agggagccgg cactgctctg    420

caccttccca aatcccagtg cacccaggaa ggacagcacc ctttcggctg tgccccagag    480

ctcctaccca ctgctggcaa atg                                            503
```

<210> SEQ ID NO 6
<211> LENGTH: 364
<212> TYPE: DNA
<213> ORGANISM: Homo sapiens

<400> SEQUENCE: 6

```
gcccttggac aaggacccga tgcccaaccc caggcctggc aagccctcgg ccccttcctt     60

ggcccttggc ccatccccag gagcctcgcc cagctggagg gctgcaccca aagcctcaga    120

cctgctgggg gcccggggcc caggggggaac cttccagggc cgagatcttc gaggcggggc   180

ccatgcctcc tcttcttcct tgaaccccat gccaccatcg cagctgcagg gatcaacgtg    240

gccagcctgg aatgggtgtc cagggagccg gcactgctct gcaccttccc aaatcccagt    300

gcacccagga aggacagcac cctttcggct gtgccccaga gctcctaccc actgctggca    360

aatg                                                                 364
```

<210> SEQ ID NO 7
<211> LENGTH: 18
<212> TYPE: DNA
<213> ORGANISM: Homo sapiens

<400> SEQUENCE: 7

```
acctacgcca cgctcatc                                                   18
```

<210> SEQ ID NO 8
<211> LENGTH: 19
<212> TYPE: DNA
<213> ORGANISM: Homo sapiens

<400> SEQUENCE: 8

```
tcattgagtg tccgctgct                                                  19
```

<210> SEQ ID NO 9
<211> LENGTH: 21
<212> TYPE: DNA
<213> ORGANISM: Homo sapiens

<400> SEQUENCE: 9

```
gtcagcaatg gtgatcttct t                                               21
```

<210> SEQ ID NO 10
<211> LENGTH: 21
<212> TYPE: DNA
<213> ORGANISM: Homo sapiens

<400> SEQUENCE: 10

```
gcagaaaatt ttcgtgctct g                                               21
```

<210> SEQ ID NO 11
<211> LENGTH: 172
<212> TYPE: PRT
<213> ORGANISM: Homo sapiens

<400> SEQUENCE: 11

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Gly Ser Thr Trp Pro Ala Trp Asn Gly Cys
65                  70                  75                  80

Pro Gly Ser Arg His Cys Ser Ala Pro Ser Gln Ile Pro Val His Pro
                85                  90                  95

Gly Arg Thr Ala Pro Phe Arg Leu Cys Pro Arg Ala Pro Thr His Cys
            100                 105                 110

Trp Gln Met Val Ser Ala Ser Gly Pro Asp Val Arg Arg Ser Ser Lys
        115                 120                 125

Ser Gln Arg Thr Ser Ser Ser Thr Ala Arg Arg Thr Ile Phe Trp Met
    130                 135                 140

Arg Arg Ala Gly His Asn Val Ser Ser Arg Glu Arg Trp Tyr Ser Leu
145                 150                 155                 160

Trp Ser Ser Ser Trp Cys Trp Arg Arg Arg Ser Glx
                165                 170
```

<210> SEQ ID NO 12
<211> LENGTH: 399
<212> TYPE: PRT
<213> ORGANISM: Homo sapiens

<400> SEQUENCE: 12

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
```

-continued

```
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu
385                 390                 395


<210> SEQ ID NO 13
<211> LENGTH: 15
<212> TYPE: PRT
<213> ORGANISM: Homo sapiens

<400> SEQUENCE: 13

Ser Ser Arg Glu Arg Trp Tyr Ser Leu Trp Ser Ser Ser Trp Cys
1               5                   10                  15
```